(12) United States Patent
Banning et al.

(10) Patent No.: US 7,381,831 B1
(45) Date of Patent: Jun. 3, 2008

(54) COLORANT COMPOUNDS

(75) Inventors: Jeffrey H. Banning, Hillsboro, OR (US); Rina Carlini, Mississauga (CA); James D. Mayo, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 11/732,745

(22) Filed: Apr. 4, 2007

(51) Int. Cl.
C07C 205/00 (2006.01)
C07C 229/00 (2006.01)

(52) U.S. Cl. .......................... 560/23; 560/22; 560/43; 560/48

(58) Field of Classification Search ................ None
See application file for complete search history.

(56) References Cited

U.S. PATENT DOCUMENTS

| | | | |
|---|---|---|---|
| 3,653,932 A | 4/1972 | Berry et al. | 106/31.29 |
| 4,390,369 A | 6/1983 | Merritt et al. | 106/31.3 |
| 4,484,948 A | 11/1984 | Merritt et al. | 106/31.3 |
| 4,658,064 A | 4/1987 | Moore et al. | 564/443 |
| 4,684,956 A | 8/1987 | Ball | 347/88 |
| 4,851,045 A | 7/1989 | Taniguchi | 106/31.31 |
| 4,889,560 A | 12/1989 | Jaeger et al. | 106/31.29 |
| 4,889,761 A | 12/1989 | Titterington et al. | 428/32.1 |
| 5,006,170 A | 4/1991 | Schwarz et al. | 106/31.3 |
| 5,013,857 A | 5/1991 | Berneth et al. | 552/110 |
| 5,151,120 A | 9/1992 | You et al. | 106/31.29 |
| 5,221,335 A | 6/1993 | Williams et al. | 524/560 |
| 5,372,852 A | 12/1994 | Titterington et al. | 427/288 |
| 5,496,879 A | 3/1996 | Griebel et al. | 524/320 |
| 5,621,022 A | 4/1997 | Jaeger et al. | 523/161 |
| 5,782,966 A | 7/1998 | Bui et al. | 106/31.43 |
| 6,174,937 B1 | 1/2001 | Banning et al. | 523/160 |
| 6,309,453 B1 | 10/2001 | Banning et al. | 106/31.29 |
| 6,576,747 B1 | 6/2003 | Carlini et al. | 534/649 |
| 6,576,748 B1 | 6/2003 | Carlini et al. | 534/649 |
| 6,590,082 B1 | 7/2003 | Banning et al. | 534/649 |
| 6,646,111 B1 | 11/2003 | Carlini et al. | 534/649 |
| 6,663,703 B1 | 12/2003 | Wu et al. | 106/31.29 |
| 6,673,139 B1 | 1/2004 | Wu et al. | 106/31.29 |
| 6,682,591 B2 | 1/2004 | Smith et al. | 106/31.58 |
| 6,696,552 B2 | 2/2004 | Mayo et al. | 534/649 |
| 6,713,614 B2 | 3/2004 | Carlini et al. | 534/649 |
| 6,755,902 B2 | 6/2004 | Banning et al. | 106/31.29 |
| 7,034,185 B2 | 4/2006 | Banning et al. | 564/443 |
| 2002/0065402 A1* | 5/2002 | Jung et al. | 534/816 |

FOREIGN PATENT DOCUMENTS

| | | |
|---|---|---|
| EP | 0187352 | 7/1986 |
| EP | 0206286 | 12/1986 |
| WO | WO 94/04619 | 3/1994 |

OTHER PUBLICATIONS

English Abstract for German Patent Publication DE 4205636AL, Aug. 1993.
English Abstract for German Patent Publication DE 4205713AL, Mar. 1996.
U.S. Appl. No. 11/732,811, filed Apr. 4, 2007, of Jeffrey Banning et al., entitled "Phase Change Inks Containing Colorant Compounds" 100 pages, not yet published.
U.S. Appl. No. 11/732,796, filed Apr. 4, 2007, of Jeffrey Banning et al., entitled "Colorant Compounds" 75 pages, not yet published.
U.S. Appl. No. 11/732,795, filed Apr. 4, 2007, of Jeffrey Banning, entitled "Phase Change Inks Containing Colorant Compounds" 95 pages, not yet published.
Chemical Reviews, Robert Clemens, "Diketene", vol. 86, No. 2, pp. 241-258, Apr. 1986.

* cited by examiner

*Primary Examiner*—Karl J Puttlitz
(74) *Attorney, Agent, or Firm*—Marylou J. Labole, Esq. LLC

(57) ABSTRACT

Disclosed is a compound of the formula

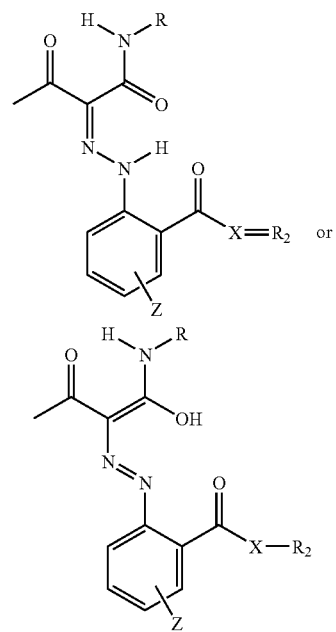

and dimers thereof, wherein R, $R_2$, X and Z are as described herein. The compounds are useful as colorants, particularly in applications such as phase change inks.

19 Claims, No Drawings

COLORANT COMPOUNDS

Cross-reference is made to the following co-pending applications:

Co-pending Application U.S. Ser. No. (not yet assigned), filed concurrently herewith, entitled "Phase Change Inks Containing Colorant Compounds," with the named inventor Jeffery H. Banning, the disclosure of which is totally incorporated herein by reference, discloses a phase change ink composition comprising a phase change ink carrier and a colorant compound.

Co-pending Application U.S. Ser. No. (not yet assigned), filed concurrently herewith, entitled "Colorant Compounds," with the named inventors Jeffery H. Banning, et al., the disclosure of which is totally incorporated herein by reference, discloses compounds of the formula

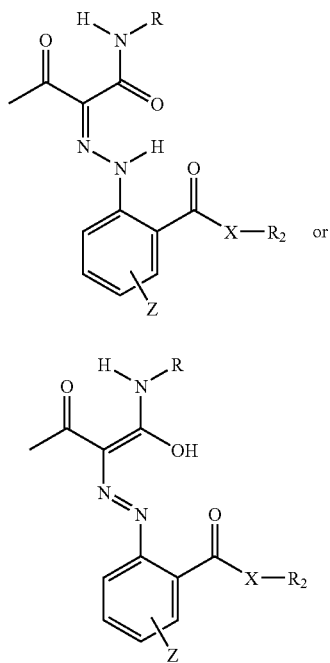

and dimers thereof.

Co-pending application U.S. Ser. No. (not yet assigned), filed concurrently herewith, entitled "Phase Change Inks Containing Colorant Compounds," with the named inventors Jeffery J. Banning, et al., the disclosure of which is totally incorporated herein by reference, discloses a phase change ink composition comprising a phase change ink carrier and a colorant compound.

BACKGROUND

The present disclosure is generally related to colorant compounds. More specifically, the present disclosure is directed to colorant compounds particularly suitable for use in hot melt or phase change inks. In embodiments, the present disclosure is directed to dimeric azo acetoacetamido colorant compounds particularly suitable for use in hot melt or phase change inks. One embodiment of the present disclosure is directed to a compound of the formula

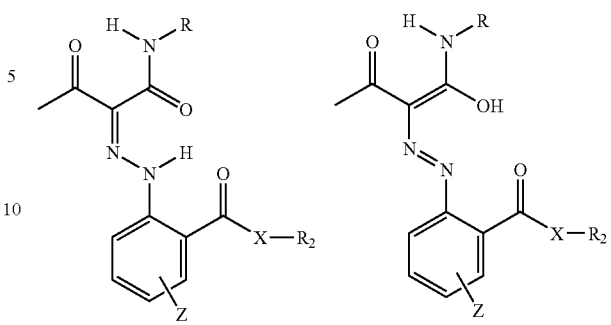

or and dimers thereof, wherein R is an N-substituted acetoacetamide;

$R_2$ is (i) an alkyl group, (ii) an alkylene group, (iii) an arylene group, (iv) an arylalkylene group, (v) an alkylarylene group, (vi) an alkyleneoxy group, (vii) an aryleneoxy group, (viii) an arylalkyleneoxy group, (ix) an alkylaryleneoxy group, (x) a polyalkyleneoxy group, (xi) a polyaryleneoxy group, (xii) a polyarylalkyleneoxy group, (xiii) a polyalkylaryleneoxy group, (xiv) a heterocyclic group, (xv) a silylene group, (xvi) a siloxane group, (xvii) a polysilylene group, or (xviii) a polysiloxane group;

X is a (i) direct bond, (ii) an oxygen atom, (iii) a nitrogen atom, (iv) a sulfur atom, (v) a group of the formula $NR_{40}$ wherein $R_{40}$ is a hydrogen atom, an alkyl group, an aryl group, an arylalkyl group, or an alkylaryl group, (vi) or a group of the formula —$CR_{50}R_{60}$—; wherein $R_{50}$ and $R_{60}$ each, independently of the other, is a hydrogen atom, an alkyl group, an aryl group, an arylalkyl group, or an alkylaryl group; and Z is optionally present and if present is a (i) hydrogen atom, (ii) a halogen atom, (iii) a nitro group, (iv) an alkyl group, (v) an aryl group, (vi) an arylalkyl group, (vii) an alkylaryl group, (viii) a group of the formula

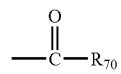

wherein $R_{70}$ is an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a heterocyclic group, a silyl group, a siloxane group, a polysilylene group, or a polysiloxante group, (ix) a sulfonyl group of the formula —$SO_2R_{80}$ wherein $R_{80}$ is a hydrogen atom, an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, or (x) a phosphoryl group of the formula —$PO_3R_{90}$ wherein $R_{90}$ is a hydrogen atom, an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group.

In general, phase change inks (sometimes referred to as "hot melt inks") are in the solid phase at ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have also been used in other printing technologies, such as gravure printing, as disclosed in, for example, U.S. Pat. No. 5,496,879 and German Patent Publications De 4205636AL and DE 4205713AL, the disclosure of each of which are totally incorporated herein by reference.

Phase change inks for color printing typically comprise a phase change ink carrier composition which is combined with a phase change ink compatible colorant. In a specific embodiment, a series of colored phase change inks can be formed by combining ink carrier compositions with compatible subtractive primary colorants. The subtractive primary colored phase change inks can comprise four component dyes, namely, cyan, magenta, yellow and black, although the inks are not limited to these four colors. These subtractive primary colored inks can be formed by using a single dye or a mixture of dyes. For example, magenta can be obtained by using a mixture of Solvent Red Dyes or a composite black can be obtained by mixing several dyes. U.S. Pat. No. 5,889,560, U.S. Pat. No. 4,889,761, and U.S. Pat. No. 5,372,852, the disclosures of each of which are totally incorporated herein by reference, teach that the subtractive primary colorants employed can comprise dyes from the classes of Color Index (C.I.) Solvent Dyes, Disperse Dyes, modified Acid and Direct Dyes, and Basic Dyes. The colorants can also include pigments, as disclosed in, for example, U.S. Pat. No. 5,221,335, the disclosure of which is totally incorporated herein by reference. U.S. Pat. No. 5,621,022, the disclosure of which is totally incorporated herein by reference, discloses the use of a specific class of polymeric dyes in phase change ink compositions.

Phase change inks have also been used for applications such as postal marking, industrial marking, and labeling.

Phase change inks are desirable for ink jet printers because they remain in a solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

Compositions suitable for use as phase change ink carrier compositions are known. Some representative examples of references disclosing such materials include U.S. Pat. No. 3,653,932, U.S. Pat. No. 4,390,369, U.S. Pat. No. 4,484,948, U.S. Pat. No. 4,684,956, U.S. Pat. No. 4,851,045, U.S. Pat. No. 4,889,560, U.S. Pat. No. 5,006,170, U.S. Pat. No. 5,151,120, U.S. Pat. No. 5,372,852, U.S. Pat, No. 5,496,879, European Patent Publication 0187352, European Patent Publication 0206286, German Patent Publication DE 4205636AL, German Patent Publication DE 4205713AL, and PCT Patent Application WO 94/04619, the disclosures of each of which are totally incorporated herein by reference. Suitable carrier materials can include paraffins, microcrystalline waxes, polyethylene waxes, ester waxes, fatty acids and other waxy materials, fatty amide containing materials, sulfonamide materials, resinous materials made from different natural sources (tall oil rosins and rosin esters, for example), and many synthetic resins, oligomers, polymers, and copolymers.

U.S. Pat. No. 6,576,747 of Rina Carlini et al., entitled "Processes for Preparing Dianthranilate Compounds and Diazopyridone Colorants," which is hereby incorporated by reference herein in its entirety, discloses a process for preparing dianthranilate compounds which comprises (a) admixing reactants as follows: (1) a diol of the formula R1(OH)2, wherein R1 is an alkylene group having at least about 20 carbon atoms, and wherein the —OH groups are primary or secondary, (2) isatoic anhydride, present in an amount of at least about 2 moles of isatoic anhydride per every one mole of diol, (3) a catalyst which is 1,4-diazabicyclo [2,2,2]octane, N,N,N', N'-tetramethylethylene diamine, or a mixture thereof, said catalyst being present in an amount of at least about 0.2 mole of catalyst per every one mole of diol, and (4) a solvent; and (b) heating the mixture thus formed to form a dianthranilate compound of the formula

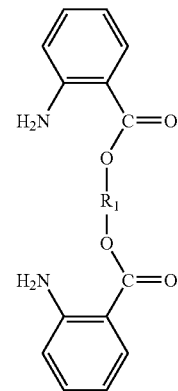

Also disclosed is a process for preparing diazopyridone colorants which comprises (I) preparing a dianthranilate compound by the aforementioned method, (II) reacting the dianthranilate compound with nitrosylsulfuric acid to form a diazonium salt, and (III) reacting the diazonium salt with a pyridine compound to form a diazopyridone compound.

U.S. Pat. No. 6,713,614 of Rina Carlini et al., entitled "Dimeric Azo Pyridone Colorants," which is hereby incorporated by reference herein in its entirety, discloses compounds of the formula

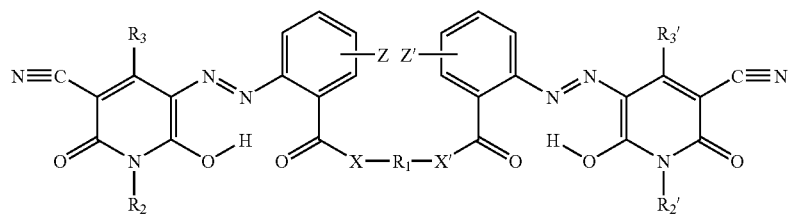

The compounds are useful as colorants, particularly in applications such as phase change inks.

U.S. Pat. No. 6,663,703 of Bo Wu et al., entitled "Phase Change Inks Containing Dimeric Azo Pyridone Colorants," which is hereby incorporated by reference herein in its entirety, discloses a phase change ink composition comprising a phase change ink carrier and a colorant compound of the formula

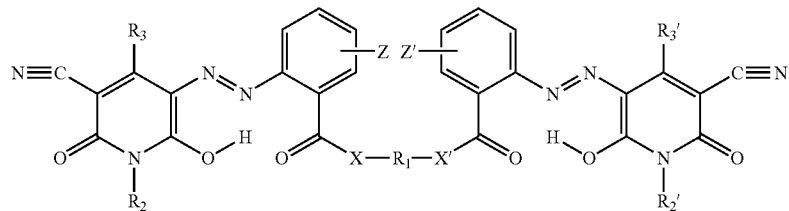

U.S. Pat. No. 6,755,902 Patent of Jeffrey H. Banning et al. entitled "Phase Change Inks Containing Azo Pyridone Colorants" which is hereby incorporated by reference herein in its entirety, discloses a phase change ink composition comprising a phase change ink carrier and a colorant compound of the formula

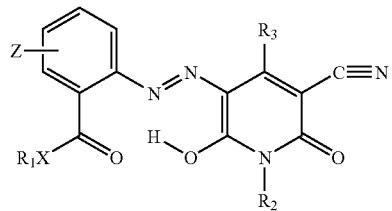

U.S. Pat. No. 6,590,082 of Jeffrey H. Banning et al. entitled "Azo Pyridone Colorants," which is hereby incorporated by reference herein in its entirety, discloses compounds of the formula

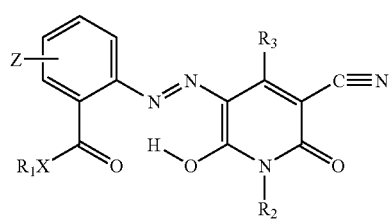

The compounds are useful as colorants, particularly in applications such as phase change inks.

U.S. Pat. No. 6,696,552 of James D. Mayo et al. entitled "Process for Preparing Substituted Pyridone Compounds," which is hereby incorporated by reference herein in its entirety, discloses a process for preparing substituted pyridone compounds which comprises (a) admixing in the absence of a solvent (1) an amine of the formula R1-NH$_2$ wherein R1 is an alkyl group, an aryl group, an arylalkyl group, or an alkylaryl group, and (2) a first ester of the formula

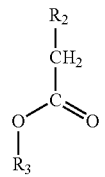

wherein $R_2$ is an electron withdrawing group and $R_5$ is an alkyl group; (b) heating the mixture containing the amine and the first ester to form as intermediate compound of the formula

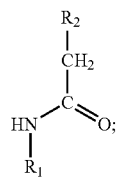

(c) admixing the intermediate compound with (1) a base and (2) a second ester of the formula

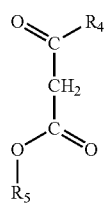

wherein R$_4$ is an alkyl group, an aryl group, an arylalkyl group, or an alkylaryl group and R$_5$ is an alkyl group, said second ester being present in a molar excess relative to the intermediate compound, said base being present in a molar excess relative to the intermediate compound, and (d) heating the mixture containing the intermediate compound, the second ester, and the base to form a pyridone compound of the formula

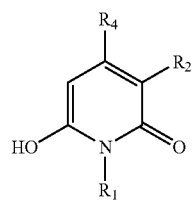

or a salt thereof. Also disclosed is a process for preparing diazopyridone colorants which comprises preparing a pyridone compound by the above process and reacting the pyridone compound with a diazonium salt to form a diazopyridone compound.

U.S. Pat. No. 6,576,748 of Rina Carlini et al. entitled "Method for Making Dimeric Azo Pyridone Colorants," which is hereby incorporated by reference herein in its entirety, discloses a process for preparing a diazopyridone compound which comprises (a) preparing a first solution comprising (1) either (A) a dianiline of the formula

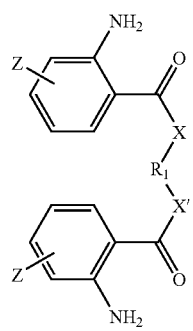

or (B) an aniline of the formula

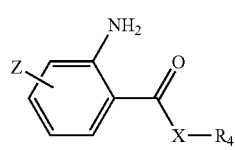

and (2) a first solvent mixture comprising (I) a solvent, (II) acetic acid, and (III) an optional second acid, said acetic acid being present in the solvent mixture in an amount of at least about 95 percent by weight of the solvent mixture, said first solution being at a temperature of about +15° C. or lower; (b) adding to the first solution nitrosylsulfuric acid, thereby forming a diazonium salt either (A) of the formula

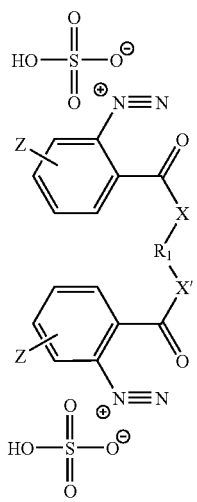

or (B) of the formula

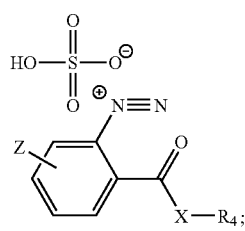

(c) preparing a second solution comprising (1) a second solvent mixture comprising water and an organic solvent soluble in or miscible in water, (2) either (A) a pyridone of the formula

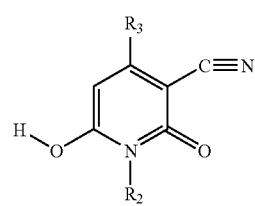

or (B) a dipyridone of the formula

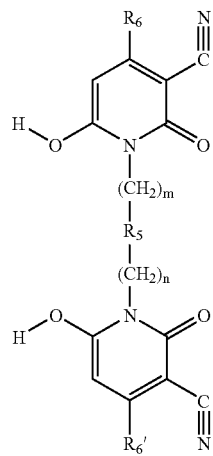

(3) a base present in an amount of at least about 3 molar equivalents of base per mole of pyridone moiety, and (4) an optional buffer salt, and (d) combining either (A) the second solution containing the dianiline and the first solution containing the pyridone, or (B) the second solution containing the aniline and the first solution containing the dipyridone to form a third solution and effect a coupling reaction to form a diazopyridone compound either (A) or the formula

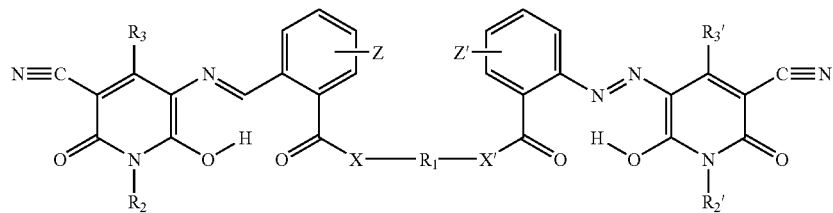

or (B) of the formula

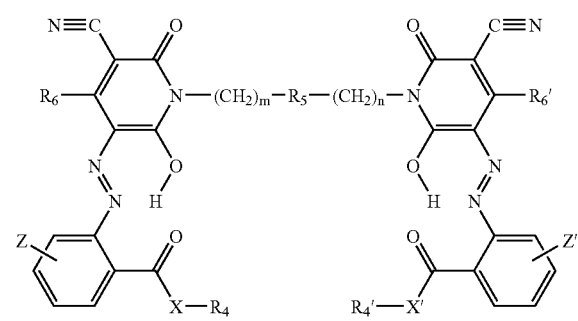

U.S. Pat. No. 6,646,111 of Rina Carlini et al. entitled "Dimeric Azo Pyridone Colorants," which is hereby incorporated by reference herein in its entirety, discloses compounds of the formula

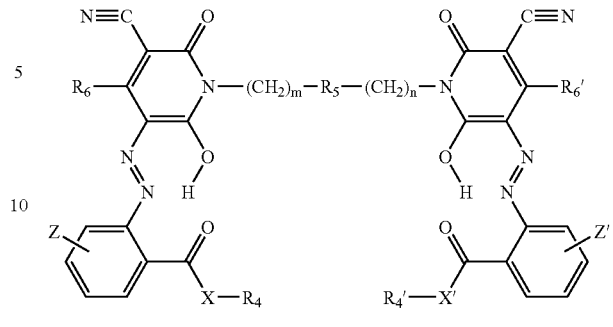

The compounds are useful as colorants, particularly in applications such as phase change inks.

U.S. Pat. No. 6,673,139 of Bo Wu et al. entitled "Phase Change Inks Containing Dimeric Azo Pyridone Colorants," which is hereby incorporated by reference herein in its entirety, discloses a phase change ink composition comprising a phase change ink carrier and a colorant compound of the formula

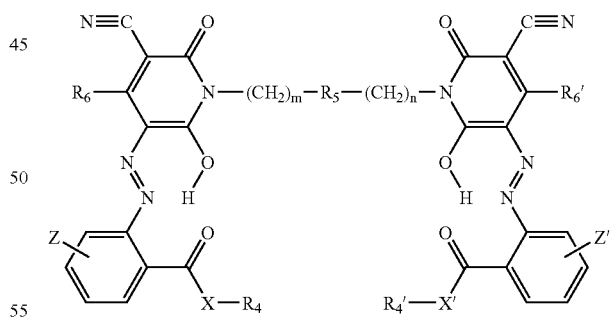

While known composition and processes are suitable for their intended purposes, a need remains for new colorant compositions, for example new yellow to orange colorant compositions. In addition, a need remains for yellow to orange colorant compositions particularly suitable for use in phase change inks. Further, a need remains for yellow to orange colorants with desirable thermal stability. Additionally, a need remains for yellow to orange colorants that exhibit minimal undesirable discoloration when exposed to elevated temperatures. There is also a need for yellow to orange colorants that exhibit a desirable brilliance. In addition, there is a need for yellow to orange colorants that exhibit a desirable hue. Further, there is a need for yellow to orange colorants that are of desirable chroma. Additionally, there is a need for yellow to orange colorants that have desirably high lightfastness characteristics. A need also remains for yellow to orange colorants that have a desirably pleasing color. In addition, a need remains for yellow to orange colorants that exhibit desirable solubility characteristics in phase change ink carrier compositions. Further, a need remains for yellow to orange colorants that enable phase change inks to be jetted at temperatures of over 135° C. while maintaining thermal stability. Further, a need remains for yellow to orange colorants for use in solid ink printers that operate with lower print head temperatures much lower than 135° C. as well as in ultraviolet radiation curable systems. Additionally, a need remains for yellow to orange colorants that enable phase change inks that generate images with low pile height. There is also a need for yellow to orange colorants that enable phase change inks that generate images that approach lithographic thin image quality. In addition, there is a need for yellow to orange colorants that exhibit oxidative stability. Further, there is a need for yellow to orange colorants that do not precipitate from phase change ink carriers. Additionally, there is a need for yellow to orange colorants that do not, when included in phases change inks, diffuse into adjacently printed inks of different colors. A need also remains for yellow to orange colorants that do not leach from media such as phase change ink carriers into tape adhesives, paper, or the like. In addition, a need remains for yellow to orange colorants that, when incorporated into phase change inks, do not lead to clogging of a phase change ink jet printhead. Further, there is a need for yellow to orange colorants that enable phase change inks that generate images with sharp edges that remain sharp over time. Additionally, there is a need for yellow to orange colorants that enable phase change inks that generate images which retain their high image quality in warm climates. Further, there is a need for yellow to orange colorants that enable phase change inks that generate images of desirably high optical density. Additionally, there is a need for yellow to orange colorants that, because of their good solubility in phase change ink carriers, enable the generation of images of low pile height without the loss of desirably high optical density. A need also remains for yellow to orange colorants that enable cost-effective inks.

The appropriate components and process aspects of the each of the foregoing may be selected for the present disclosure in embodiments thereof.

SUMMARY

In embodiments, the present disclosure is directed to a compound of the formula

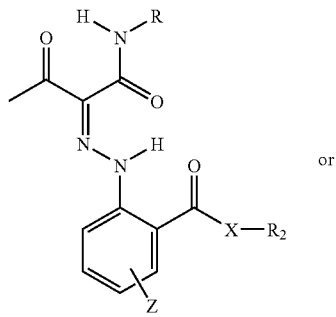

or

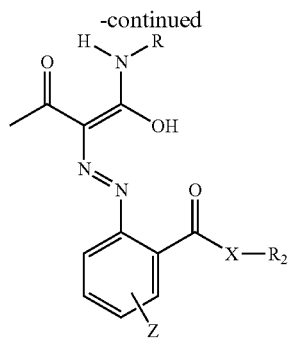

and dimers thereof, wherein R is an N-substituted acetoacetamide;

$R_2$ is (i) an alkyl group; (ii) an alkylene group, (iii) an arylene group, (iv) an arylalkylene group, (v) an alkylarylene group, (vi) an alkyleneoxy group, (vii) an aryleneoxy group, (viii) an arylalkyleneoxy group, (ix) an alkylaryleneoxy group, (x) a polyalkyleneoxy group, (xi) a polyaryleneoxy group, (xii) a polyarylalkyleneoxy group, (xiii) a polyalkylaryleneoxy group, (xiv) a heterocyclic group, (xv) a silylene group, (xvi) a siloxane group, (xvii) a polysilylene group, or (xviii) a polysiloxane group;

X and X', if X' is present, is a (i) direct bond, (ii) an oxygen atom, (iii) a nitrogen atom, (iv) a sulfur atom, (v) a group of the formula —$NR_{40}$— wherein $R_{40}$ is a hydrogen atom, an alkyl group, an aryl group, an arylalkyl group, or an alkylaryl group, (vi) or a group of the formula —$CR_{50}R_{60}$—; wherein $R_{50}$ and $R_{60}$ each, independently of the other, is a hydrogen atom, an alkyl group, an aryl group, an arylalkyl group, or an alkylaryl group, wherein two or more substituents can be joined together to form a ring and wherein X and X' can be the same as each other or different from each other; and Z and Z' are each optionally present and if present are each independently selected from a (i) hydrogen atom, (ii) a halogen atom, (iii) a nitro group, (iv) an alkyl group, (v) an aryl group, (vi) an arylalkyl group, (vii) an alkylaryl group, (viii) a group of the formula

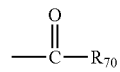

wherein $R_{70}$ is an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a heterocyclic group, a silyl group, a siloxane group, a polysilylene group, or a polysiloxane group, (ix) a sulfonyl group of the formula —$SO_2R_{80}$ wherein $R_{80}$ is a hydrogen atom, an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, or (x) a phosphoryl group of the formula —$PO_3R_{90}$ wherein $R_{90}$ is a hydrogen atom, an alkyl group, an aryl group, an arylalkyl group, an alkylaryl group, an alkoxy group, an aryloxy group, an arylalkyloxy group, an alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, wherein two or more substituents can be joined together to form a ring, and wherein Z and Z' can be the same as each other or different from each other;

wherein Z and X can be joined together to form a ring and wherein Z' and X' can be joined together to form a ring.

In embodiments, the present disclosure includes dimeric compounds of the formula

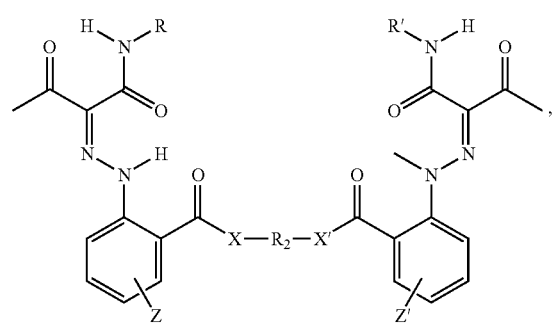

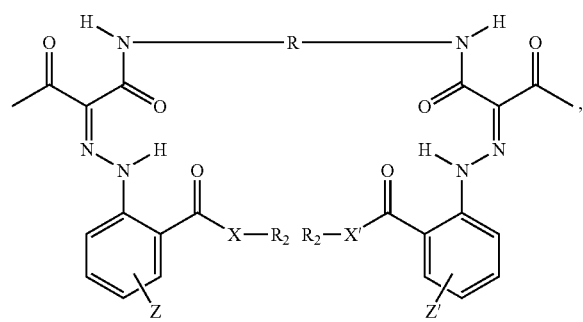

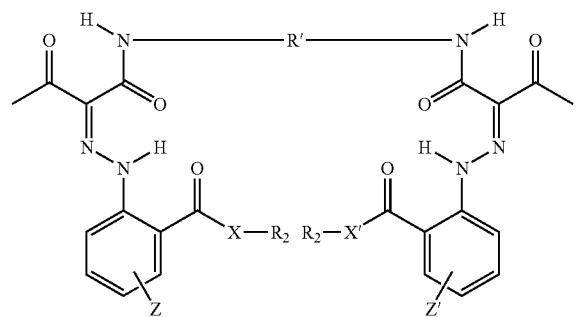

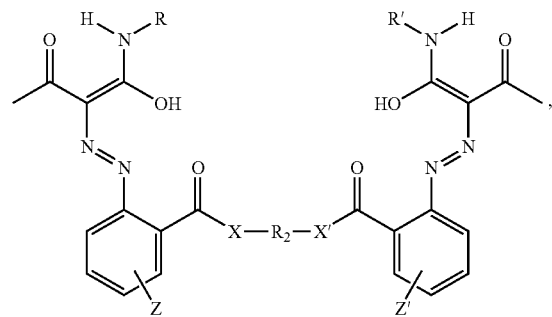

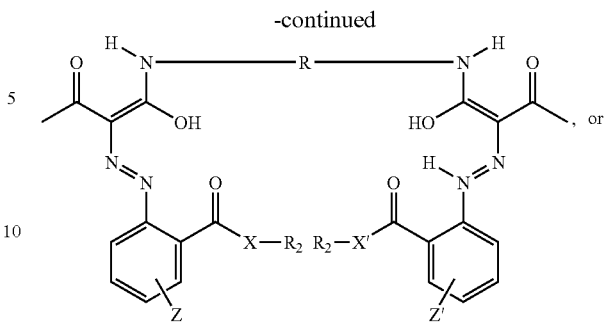

, or

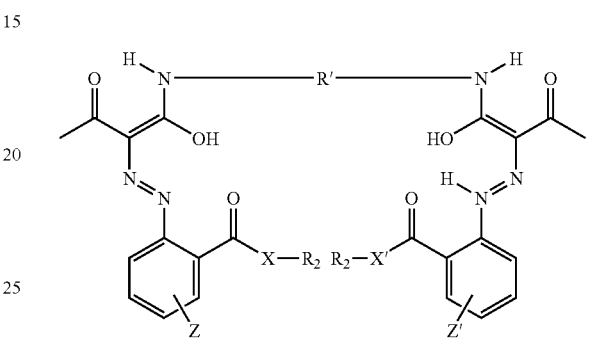

wherein R, R', $R_2$, X, X', Z and Z' are as described herein.

DETAILED DESCRIPTION

The present disclosure is directed to colorant compounds particularly suitable for use in hot melt or phase change inks. In embodiments, the present disclosure is directed to dimeric azo acetoacetamido colorant compounds particularly suitable for use in hot melt or phase change inks. One embodiment of the present disclosure is directed to compounds and dimerized compounds of the formula

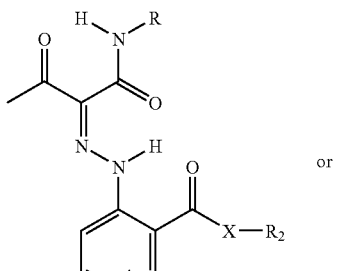

or

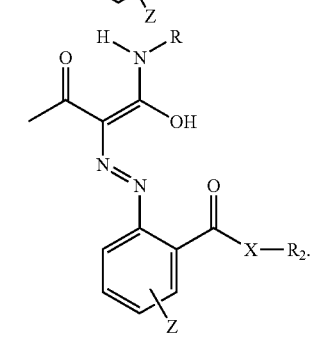

or

While not wishing to be bound by theory, as with pyrazolone and azopyridone dyes, it is noted that acetoacetamido dyes exist predominantly in the hydrazone form after synthesis. That is, acetoacetamido dyes initially form the enol (referred to as the diazo form) when the coupling reaction takes place and then tautomerize to the keto form (referred to as the hydrazone form). However, as with pyrazolone and azopyridone dyes, the acetoacetamido compounds can exist in both forms. For example, under certain environmental conditions (for example, in certain solvents), the acetoacetamido dye can revert back to the diazo form.

The compounds can be dimerized through R or R'. For example, in embodiments, dimers of the keto form (hydrazone form)

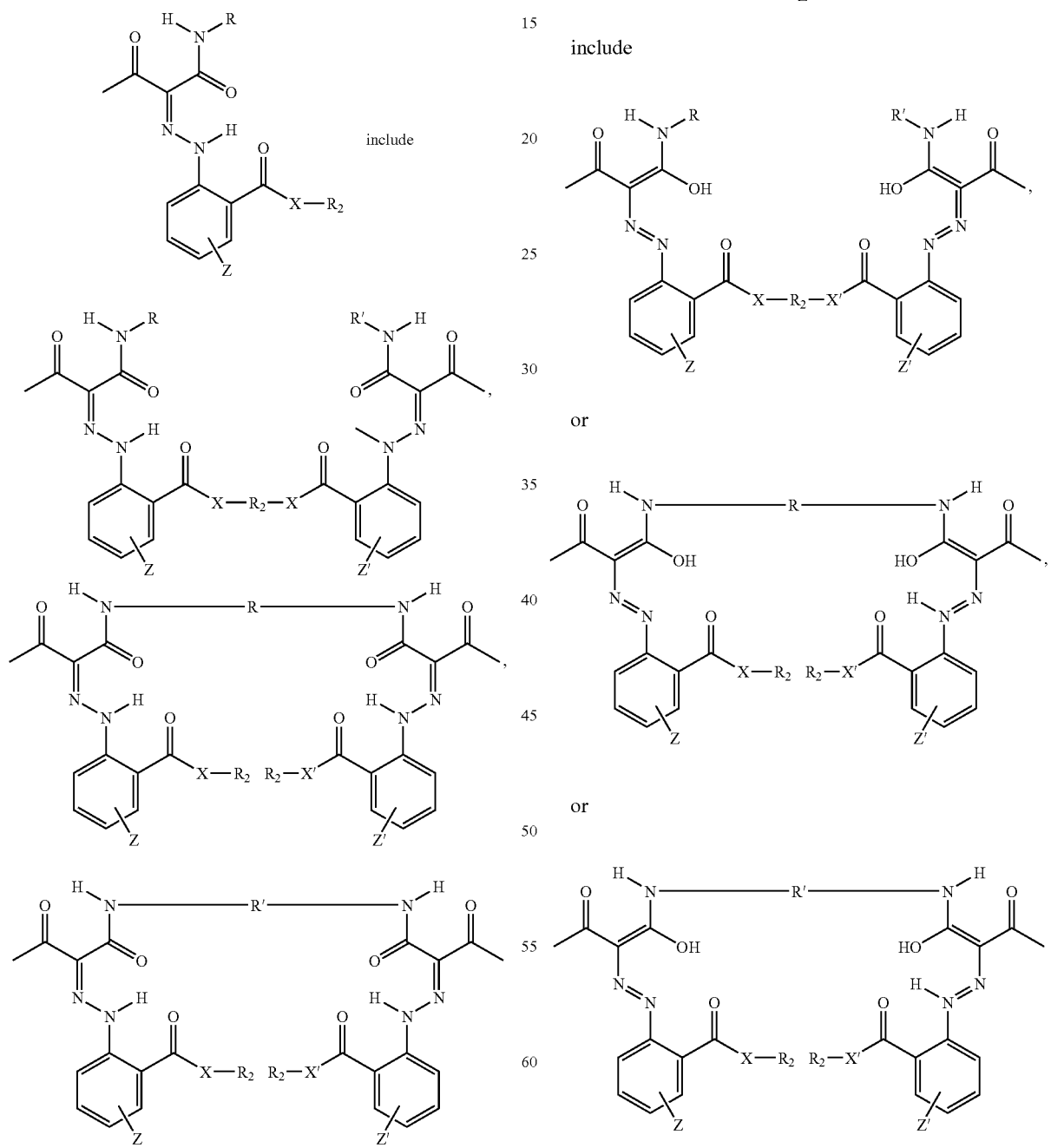

include

For example, in embodiments, dimers of the enol form (diazo form)

wherein R and R', if R' is present, is an N-substituted acetoacetamide; for example, in embodiments, R and R' is, for example 2-ethylhexylacetoacetamide, dodecylanilineacetoacetamide; Guerbet-acetoacetamide, or p-hydroxyethyla-nilino-acetaoacetamide, and the like.

A Guerbet alcohol refers to a beta-branched primary alcohol of the general formula

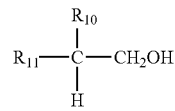

wherein $R_{10}$ and $R_{11}$ each, independently of the other, are alkyl groups (including linear, branched, saturated, unsaturated, cyclic, and substituted alkyl groups, and wherein hetero atoms, such as oxygen, nitrogen, sulfur, silicon, phosphorus, boron, and the like, either may or may not be present in the alkyl group), typically with from about 1 to about 22 carbon atoms, or about 1 to about 12 carbon atoms, or about 1 to about 7 carbon atoms, although the number of carbon atoms can be outside of these ranges, aryl groups (including substituted aryl groups), typically with from about 6 to about 30 carbon atoms, or from about 6 to about 15 carbon atoms, or from about 6 to about 12 carbon atoms, although the number of carbon atoms can be outside of these rangers, arylalkyl groups (including substituted arylalkyl groups), typically with from about 7 to about 30 carbon atoms, or from about 7 to about 15 carbon atoms, or from about 7 to about 12 carbon atoms, although the number of carbon atoms can be outside of these ranges, such as benzyl or the like, alkylaryl groups (including substituted alkylaryl groups), typically with from about 7 to about 30 carbon atoms, or from about 7 to about 15 carbon atoms, or from about 7 to about 12 carbon atoms, although the number of carbon atoms can be outside of these ranges, alkoxy groups (including substituted alkoxy groups, and wherein hetero atoms, such as oxygen, nitrogen, sulfur, silicon, phosphorus, boron, and the like can be present in the alkoxy group), typically with from about 1 to about 22 carbons, or from about 1 to about 12 carbons atoms, or from about 1 to about 7 carbon atoms, although the number of carbon atoms can be outside of these ranges, polyalkyleneoxy groups (including substituted polyalkyleneoxy groups), such as polyethyleneoxy groups, polypropyleneoxy groups, polybutyleneoxy groups, and the like, typically with from about 3 to about 60 repeat alkyleneoxy units, or from about 3 to about 30 repeat alkyleneoxy units, or from about 3 to about 20 repeat alkyleneoxy units, although the number of repeat alkyleneoxy units can be outside of these ranges, although the number of repeat alkyleneoxy units can be outside of these ranges, wherein $R_{10}$ and $R_{11}$ can be joined together to form a ring, and wherein the substituents on the substituted alkyl, aryl, arylalkyl, alkylaryl, alkoxy, and polyalkyleneoxy groups can be, but are not limited to, hydroxy groups, amine groups, ammonium groups, pyridine groups, pyridinium groups, ether groups, ester groups, amide groups, carbonyl groups, mixtures thereof, and the like, wherein two or more substituents can be joined together to form a ring.

and wherein a Guerbet acetoacetamide refers to an acetoacetamide derived from a Guerbet amine (the Guerbet amine being derived from a Guerbet alcohol) and an acetonitrile.

wherein in embodiments the number of carbon atoms in R plus $R_2$ is at least about 12;

$R_2$ is (i) an alkyl group (including linear, branched, saturated, unsaturated, cyclic, unsubstituted, and substituted alkyl groups, and wherein hetero atoms, such as oxygen, nitrogen, sulfur, silicon, phosphorus, boron, and the like either may or may not be present in the alkyl group), in one embodiment with at least about 1 to about 50 carbon atoms, in another embodiment with at least about 2 to about 20 carbon atoms, in another embodiment with at least about 4 to about 12 carbon atoms, although the number of carbon atoms can be outside of these ranges;

(ii) an alkylene group, (including linear, branched, saturated, unsaturated, cyclic, an alkylene group including aliphatic cyclic moieties therein, unsubstituted, and substituted alkylene groups, and wherein hetero atoms, such as oxygen, nitrogen, sulfur, silicon, phosphorus, boron, and the like either may or may not be present in the alkylene group), in one embodiment with at least 1 carbon atom, in another embodiment with at least about 10 carbon atoms, in yet another embodiment with at least about 20 carbon atoms, in still another embodiment with at least about 36 carbon atoms, in one embodiment with no more than about 200 carbon atoms, in another embodiment with no more than about 100 carbon atoms, in another embodiment, with no more than about 60 carbon atoms, in yet another embodiment with no more than about 40 carbon atoms, although the number of carbon atoms can be outside of these ranges, in yet another embodiment $R_2$ is a branched alkylene group having 36 carbon atoms and optionally including unsaturations and cyclic groups;

(iii) an arylene group (including unsubstituted and substituted arylene groups, and wherein hetero atoms, such as oxygen, nitrogen, sulfur, silicon, phosphorus, boron, and the like either may or may not be present in the arylene group), in one embodiment with at least about 6 carbon atoms, in yet another embodiment with at least about 13 carbon atoms, in still another embodiment with at least about 18 carbon atoms, and in yet another embodiment with at least about 23 carbon atoms, and in one embodiment with no more than about 100 carbon atoms, in another embodiment with no more than about 75 carbon atoms, and in yet another embodiment with no more than about 50 carbon atoms, although the number of carbon atoms can be outside of these ranges;

(iv) an arylalkylene group (including unsubstituted and substituted arylalkylene groups, and wherein hetero atoms, such as oxygen, nitrogen, sulfur, silicon, phosphorus, boron, and the like either may or may not be present in either the aryl or the alkyl portion of the arylalkylene group), in one embodiment with at least about 7 carbon atoms, in another embodiment with at least about 18 carbon atoms, in yet another embodiment with at least about 30 carbon atoms, in another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges;

(v) an alkylarylene group, (including unsubstituted and substituted alkylarylene groups, and wherein hetero atoms, such as oxygen, nitrogen, sulfur, silicon, phosphorus, boron, and the like either may or may not be present in either the alkyl or the aryl portion of the alkylarylene group), in one embodiment with at least about 7 carbon atoms, in yet another embodiment with at least about 18 carbon atoms, in yet another embodiment with at least about 30 carbon atoms, in another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges;

(vi) an alkyleneoxy group, (including linear, branched, saturated, unsaturated cyclic, unsubstituted, and substituted alkyleneoxy groups, and wherein hetero atoms, such as oxygen, nitrogen, sulfur, silicon, phosphorus, boron, and the like either may or may not be present in the alkyl portion of the alkyleneoxy group), in one embodiment with at least 1 carbon atom, in another embodiment with at least about 10 carbon atoms, in another embodiment with at least about 20 carbon atoms, and in one embodiment with no more than about 200 carbon atoms, in another embodiment with no more than about 100 carbon atoms, in still another embodiment with no more than about 60 carbon atoms;

(vii) an aryleneoxy group, (including unsubstituted and substituted aryleneoxy groups, and wherein hetero atoms, such as oxygen, nitrogen, sulfur, silicon, phosphorus, boron, and the like either may or may not be present in the aryl portion of the aryleneoxy group), in one embodiment with at least about 6 carbon atoms, in another embodiment with at least about 13 carbon atoms, in still another embodiment with at least about 18 carbon atoms, and in one embodiment with no more than about 100 carbon atoms, in another embodiment with no more than about 75 carbon atoms, and in yet another embodiment with no more than about 50 carbon atoms, although the number of carbon atoms can be outside of these ranges;

(viii) an arylalkyleneoxy group, (including unsubstituted and substituted arylalkyleneoxy groups, and wherein hetero atoms, such as oxygen, nitrogen, sulfur, silicon, phosphorus, boron, and the like either may or may not be present in the either the aryl or the alkyl portion of the arylalkyleneoxy group), in one embodiment with at least about 7 carbon atoms, in yet another embodiment with at least about 18 carbon atoms, in yet another embodiment with at least about 30 carbon atoms, in another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges;

(ix) an alkylaryleneoxy group, (including unsubstituted and substituted alkylaryleneoxy groups, and wherein hetero atoms, such as oxygen, nitrogen, sulfur, silicon, phosphorus, boron, and the like either may or may not be present in the alkyl or the aryl portion of the alkylaryleneoxy group), in one embodiment with at least about 7 carbon atoms, in yet another embodiment with at least about 18 carbon atoms, in yet another embodiment with at least about 30 carbon atoms, in another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges;

(x) a polyalkyleneoxy group, wherein the alkyl portion of the repeat alkyleneoxy groups typically has from about 1 to about 12 carbon atoms, although the number of carbon atoms can be outside of these ranges, such as a polyethyleneoxy group, a polypropyleneoxy group, a polybutyleneoxy group, or the like, and wherein the number of repeat alkyleneoxy groups typically is from about 2 to about 50 repeat alkyleneoxy groups, although the number of repeat units can be outside of these ranges;

(xi) a polyaryleneoxy group, wherein the aryl portion of the repeat aryleneoxy groups typically has from about 6 to about 14 carbon atoms, although the number of carbon atoms can be outside of these ranges, such as a polyphenyleneoxy group, a polynaphthaleneoxy group, a polyphenanthreneoxy group, or the like, and wherein the number of repeat aryleneoxy groups typically is from about 2 to about 20 repeat aryleneoxy groups, although the number of repeat units can be outside of these ranges;

(xii) a polyarylalkyleneoxy group, wherein the arylalkyl portion of the repeat arylalkyleneoxy groups typically has from about 7 to about 50 carbon atoms, although the number of carbon atoms can be outside of these ranges, such as a polybenzyleneoxy group, a polyphenylethyleneoxy group, or the like, and wherein the number of repeat arylalkyleneoxy groups typically is from about 2 to about 20 repeat arylalkyleneoxy groups, although the number of repeat units can be outside of these ranges;

(xiii) a polyalkylaryleneoxy group, wherein the alkylaryl portion of the repeat alkylaryleneoxy groups typically has from about 7 to about 50 carbon atoms, although the number of carbon atoms can be outside of these ranges, such as a polytolueneoxy group or the like, and wherein the number of repeat alkylaryleneoxy groups typically is from about 2 to about 20 repeat alkylaryleneoxy groups, although the number of repeat units can be outside of these ranges;

(xiv) a heterocyclic group, (including unsubstituted and substituted heterocyclic groups), typically with from about 2 to about 12 carbon atoms, and typically with from about 4 to about 18 ring atoms, although the number of carbon atoms and the number of ring atoms can be outside of these ranges, wherein the heteroatoms in the heterocyclic groups can be (but are not limited to) nitrogen, oxygen, sulfur, silicon, phosphorus, boron, and the like, as well as mixtures thereof;

(xv) a silylene group, (including unsubstituted and substituted silylene groups);

(xvi) a siloxane group, (including unsubstituted and substituted siloxane groups);

(xvii) a polysilylene group, (including unsubstituted and substituted polysilylene groups), typically with from 2 to about 100 repeat silylene units, or (xvii) a polysiloxane group (including unsubstituted and substituted polysiloxane groups), typically with from 2 to about 200 repeat siloxane units, although the number of repeat siloxane units can be outside of this range, wherein the substituents on the substituted alkylene, arylene, arylalkylene, alkylarylene, alkyleneoxy, aryleneoxy, arylalkyleneoxy, alkylaryleneoxy, polyalkyleneoxy, polyaryleneoxy, polyarylalkyleneoxy, polyalkylaryleneoxy, heterocyclic, silylene, siloxy, polysilylene, and polysiloxy groups are hydroxy groups, halogen atoms, cyano groups, ether groups, aldehyde groups, ketone groups, carboxylic acid groups, ester groups, amide groups, carbonyl groups, thiocarbonyl groups, sulfate groups, sulfonate groups, sulfide groups, sulfoxide groups, phosphate groups, nitrile groups, mercapto groups, nitro groups, nitroso groups, sulfone groups, acyl groups, acid anhydrde groups, azide groups, cyanato groups, isocyanato groups, thiocyanato groups, isothiocyanato groups, mixtures thereof, and the like, wherein the substituents on the silylene, siloxy, polysilylene, and polysiloxy groups can also be alkyl groups, aryl groups, arylalkyl groups, and alkylaryl groups, wherein two or more substituents can be joined together to form a ring.

Some specific examples of suitable $R_2$ groups include (but are not limited to) a menthyl group of the formula

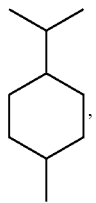

n-hexanediyl, of the formula —(CH$_2$)$_6$—, n-octanediyl, of the formula —(CH$_2$)$_8$—, n-decanediyl, of the formula —(CH$_2$)$_{10}$—, n-dodecanediyl, of the formula —(CH$_2$)$_{12}$—, 3-methyl-1,5-pentanediyl, of the formula

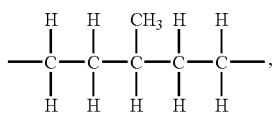

1,4-cyclohexanedimethylene, of the formula (which is not intended to be limited to any particularly stereochemistry and includes all cis and trans isomers)

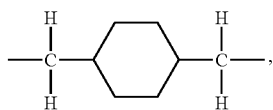

4,4'-isopropylidenedicyclohexanediyl, of the formula (which is not intended to be limited to any particular stereochemistry and includes all cis and trans isomers)

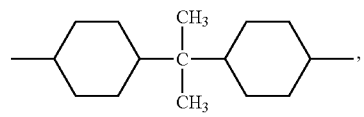

4,4'-bicyclohexyanediyl, of the formula (which is not intended to be limited to any particular stereochemistry and includes all cis and trans isomers)

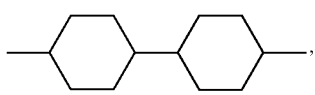

a branched alkylene group having 36 carbon atoms, including isomers of the formula

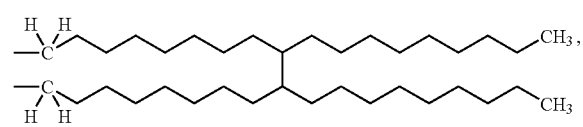

a branched alkylene group having 36 carbon atoms, including isomers of the formula and other branched alkylene isomers (which may include unsaturations and cyclic groups), 4,8-bis(methylene)tricyclo[5210$^{2,6}$]decanediyl, of the formula (which is not intended to be limited to any particular stereochemistry and includes all cis and trans isomers)

and the like.

X and X' if X' is present, are each independently of the other (i) a direct bond, (ii) an oxygen atom, (iii) a sulfur atom, (iv) a group of the formula —NR$_{40}$— wherein R$_{40}$ is a hydrogen atom, an alkyl group (including linear, branched, saturated, unsaturated, cyclic, unsubstituted, and substituted alkyl groups, and wherein hetero atoms, such as oxygen, nitrogen, sulfur, silicon, phosphorus, boron, and the like either may or may not be present in the alkyl group), typically with from 1 to about 50 carbon atoms, or from about 2 to about 20 carbon atoms, or from about 4 to about 12 carbon atoms, although the number of carbon atoms can be outside of these ranges, an aryl group (including substituted aryl groups, and wherein hetero atoms, such as oxygen, nitrogen, sulfur, silicon, phosphorus, boron, and the like either may or may not be present in the aryl group), typically with from about 6 to about 50 carbon atoms, or from about 6 to about 20 carbon atoms, or from about 6 to about 10 carbon atoms, although the number of carbon atoms can be outside of these ranges, an arylalkyl group (including substituted arylalkyl groups, and wherein hetero atoms, such as oxygen, nitrogen, sulfur, silicon, phosphorus, boron, and the like either may or may not be present in either the aryl portion or the alkyl portion of the arylalkyl group), typically with from about 7 to about 100 carbon atoms, or from about 7 to about 50 carbon atoms, or from about 7 to about 20 carbon atoms, although the number of carbon atoms can be outside of these ranges, or an alkylaryl group (including substituted alkylaryl groups, and wherein hetero atoms, such as oxygen, nitrogen, sulfur, silicon, phosphorus, boron, and the like either may or may not be present in the alkyl portion or the aryl portion of the alkylaryl group), typically with from about 7 to about 100 carbon atoms, or from about 7 to about 50 carbon atoms, or from about 7 to about 20 carbon atoms, although the number of carbon atoms can be outside of these ranges, or (v) a group of the formula —$CR_{50}R_{60}$— wherein $R_{50}$ and $R_{60}$ each, independently of the other, is a hydrogen atom, an alkyl group (including linear, branched, saturated, unsaturated, cyclic, unsubstituted, and substituted alkyl groups, and wherein hetero atoms, such as oxygen, nitrogen, sulfur, silicon, phosphorus, boron, and the like either may or may not be present in the alkyl group), typically with from 1 to about 50 carbon atoms, or from about 2 to about 20 carbon atoms, or from about 4 to about 12 carbon atoms, although the number of carbon atoms can be outside of these ranges, an aryl group (including substituted aryl groups, and wherein hetero atoms, such as oxygen, nitrogen, sulfur, silicon, phosphorus, boron, and the like either may or may not be present in the aryl group), typically with from about 6 to about 50 carbon atoms, or from about 6 to about 20 carbon atoms, or from about 6 to about 10 carbon atoms, although the number of carbon atoms can be outside of these ranges, an arylalkyl group (including substituted arylalkyl groups, and wherein hetero atoms, such as oxygen, nitrogen, sulfur, silicon, phosphorus, boron, and the like either may or may not be present in the aryl portion or the alkyl portion of the arylalkyl group), typically with from about 7 to about 100 carbon atoms, or from about 7 to about 50 carbon atoms, or from about 7 to about 20 carbon atoms, although the number of carbon atoms can be outside of these ranges, or an alkylaryl group (including substituted alkylaryl groups, and wherein hetero atoms, such as oxygen, nitrogen, sulfur, silicon, phosphorus, boron, and the like either may or may not be present in the alkyl portion or the aryl portion of the alkylaryl group), typically with from about 7 to about 100 carbon atoms, or from about 7 to about 50 carbon atoms, or from about 7 to about 20 carbon atoms, although the number of carbon atoms can be outside of these ranges, wherein the substituents on the substituted alkyl, aryl, arylalkyl, and alkylaryl groups can be (but are not limited to) hydroxy groups, halogen atoms, amine groups, imine groups, ammonium groups, pyridine groups, pyridinium groups, ether groups, aldehyde groups, ester groups, amide groups, carbonyl groups, thiocarbonyl groups, sulfate groups, sulfonate groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like, wherein two or more substituents can be joined together to form a ring and wherein X and X' can be the same as each other or different from each other.

Z and Z' are each optionally present, and if present are each, independently of the other (i) a hydrogen atom, (ii) a halogen atom, including fluorine, chlorine, bromine, and iodine, (iii) a nitro group, (iv) an alkyl group (including linear, branched, saturated, unsaturated, cyclic, unsubstituted, and substituted alkyl groups, and wherein hetero atoms, such as oxygen, nitrogen, sulfur, silicon, phosphorus, boron, and the like either may or may not be present in the alkyl group), typically with from 1 to about 50 carbon atoms, or about 1 to about 20 carbon atoms, or from about 1 to about 10 carbon atoms, although the number of carbon atoms can be outside of these ranges, (v) an aryl group (including substituted aryl groups, and wherein hetero atoms, such as oxygen, nitrogen, sulfur, silicon, phosphorus, boron, and the like either may or may not be present in the aryl group), typically with from about 6 to about 50 carbon atoms, or from about 6 to about 14 carbon atoms, or from about 6 to about 10 carbon atoms, although the number of carbon atoms can be outside of these ranges, (vi) an arylalkyl group (including substituted arylalkyl groups, and wherein hetero atoms, such as oxygen, nitrogen, sulfur, silicon, phosphorus, boron, and the like either may or may not be present in the aryl portion or the alkyl portion of the arylalkyl group), typically with from about 7 to about 50 carbon atoms, or about 7 to about 25 carbon atoms, or from about 7 to about 15 carbon atoms, although the number of carbon atoms can be outside of these ranges, (vii) an alkylaryl group (including substituted alkylaryl groups, and wherein hetero atoms, such as oxygen, nitrogen, sulfur, silicon, phosphorus, boron, and the like either may or may not be present in the alkyl portion or the aryl portion of the alkylaryl group), typically with from about 7 to about 50 carbon atoms, or from about 7 to about 25 carbon atoms, or from about 7 to about 15 carbon atoms, although the number of carbon atoms can be outside of these ranges, (viii) a group of the formula

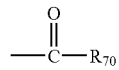

wherein $R_{70}$ is an alkyl group (including linear, branched, saturated, unsaturated, cyclic, unsubstituted, and substituted alkyl groups, and wherein hetero atoms, such as oxygen, nitrogen, sulfur, silicon, phosphorus, boron, and the like either may or may not be present in the alkyl group), typically with form 1 to about 50 carbon atoms, or from about 1 to about 20 carbon atoms, or from about 1 to about 10 carbon atoms, although the number of carbon atoms can be outside of these ranges, an aryl group (including substituted aryl groups, and wherein hetero atoms, such as oxygen, nitrogen, sulfur, silicon, phosphorus, boron, and the like either may or may not be present in the aryl group), typically with from about 6 to about 50 carbon atoms, or from about 6 to about 20 carbon atoms, or from about 6 to about 14 carbon atoms, although the number of carbon atoms can be outside of these ranges, an arylalkyl group (including substituted arylalkyl groups, and wherein hetero atoms, such as oxygen, nitrogen, sulfur, silicon, phosphorus, boron, and the like either may or may not be present in the aryl portion or the alkyl portion of the arylalkyl group), typically with from about 7 to about 50 carbon atoms, or from about 7 to about 25 carbon atoms, or from about 7 to about 15 carbon atoms, although the number of carbon atoms can be outside of these ranges, an alkylaryl group (including substituted alkylaryl groups, and wherein hetero atoms, such as oxygen, nitrogen, sulfur, silicon, phosphorus, boron, and the like either may or may not be present in the alkyl portion or the aryl portion of the alkylaryl group), typically with from about 7 to about 50 carbon atoms, or from about 7 to about 25 carbon atoms, or from about 7 to about 15 carbon atoms, although the number of carbon atoms can be outside of these ranges, an alkoxy group (including linear, branched, saturated, unsaturated, cyclic, unsubstituted, and substituted alkoxy groups, and wherein hetero atoms, such as oxygen, nitrogen, sulfur, silicon, phosphorus, boron, and the like either may or may not be present in the alkyl portion of the alkoxy group), typically with from about 1 to about 50 carbon atoms, or from about 4 to about 20 carbon atoms, or from about 8 to about 12 carbon atoms, although the number of carbon atoms can be outside of these ranges, an aryloxy group (including substituted aryloxy groups, and wherein hetero atoms, such as oxygen, nitrogen, sulfur, silicon, phosphorus, boron, and the like either may or may not be present in the aryl portion of the aryloxy group), typically with from about 6 to about 50 carbon atoms, or from about 6 to about 20 carbon atoms, or from about 6 to about 14 carbon atoms, although the number of carbon atoms can be outside of these ranges, an arylalkyloxy group (including substituted arylalkyloxy groups, and wherein hetero atoms, such as oxygen, nitrogen, sulfur, silicon, phosphorus, boron, and the like either may or may not be present in the aryl portion or the alkyl portion of the arylalkyloxy group), typically with from about 7 to about 50 carbon atoms, or from about 7 to about 25 carbon atoms, or from about 7 to about 15 carbon atoms, although the number of carbon atoms can be outside of these ranges, an alkylaryloxy group (including substituted alkylaryloxy groups, and wherein hetero atoms, such as oxygen, nitrogen, sulfur, silicon, phosphorus, boron, and the like either may or may not be present in the alkyl portion or the aryl portion of the of the alkylaryloxy group), typically with from about 7 to about 50 carbon atoms, or from about 7 to about 25 carbon atoms, or from about 7 to about 15 carbon atoms, although the number of carbon atoms can be outside of these ranges, a polyalkyleneoxy group, wherein the alkyl portion of the repeat alkyleneoxy groups typically has from about 1 to about 12 carbon atoms, although the number of carbon atoms can be outside of these ranges, such as a polyethyleneoxy group, a polypropyleneoxy group, a polybutyleneoxy group, or the like, and wherein the number of repeat alkyleneoxy groups typically is from about 2 to about 50 repeat alkyleneoxy groups, although the number of repeat units can be outside of these ranges, a polyaryleneoxy group, wherein the aryl portion of the repeat aryleneoxy groups typically has from about 6 to about 14 carbon atoms, although the number of carbon atoms can be outside of these ranges, such as a polyphenyleneoxy group, a polynaphthaleneoxy group, a polyphenanthreneoxy group, or the like, and wherein the number of repeat aryleneoxy groups typically is from about 2 to about 20 repeat aryleneoxy groups, although the number of repeat units can be outside of these ranges, a polyarylalkyleneoxy group, wherein the arylalkyl portion of the repeat arylalkyleneoxy groups typically has from about 7 to about 50 carbon atoms, although the number of carbon atoms can be outside of these ranges, such as a polybenzyleneoxy group, a polyphenylethyleneoxy group, or the like, and wherein the number of repeat arylalkyleneoxy groups typically is from about 2 to about 20 repeat arylalkyleneoxy groups, although the number of repeat units can be outside of these ranges, a polyalkylaryleneoxy group, wherein the alkylaryl portion of the repeat alkylaryleneoxy groups typically has from about 7 to about 50 carbon atoms, although the number of carbon atoms can be outside of these ranges, such as a polytolueneoxy group or the like, and wherein the number of repeat alkylaryleneoxy groups typically is from about 2 to about 20 repeat alkylaryleneoxy groups, although the number of repeat units can be outside of these ranges, a heterocyclic group (including unsubstituted and substituted heterocyclic groups), typically with from about 2 to about 12 carbon atoms, and typically with from about 4 to about 18 ring atoms, although the number of carbon atoms and the number of ring atoms can be outside of these ranges, wherein the heteroatoms in the heterocyclic groups can be (but are not limited to) nitrogen, oxygen, sulfur, silicon, phosphorus, boron, and the like, as well as mixtures thereof, a silyl group (including unsubstituted and substituted silyl groups), a siloxane group (including unsubstituted and substituted siloxane groups), a polysilylene group (including unsubstituted and substituted polysilylene groups), typically with from 2 to about 100 repeat silylene units, or a polysiloxane group (including unsubstituted and substituted polysiloxane groups), typically with from 2 to about 200 repeat siloxane units, although the number of repeat siloxane units can be outside of this range, (ix) a sulfonyl group of the formula $-SO_2R_{80}$, wherein $R_{80}$ is a hydrogen atom, an alkyl group (including linear, branched, saturated, unsaturated, cyclic, unsubstituted, and substituted alkyl groups, and wherein hetero atoms, such as oxygen, nitrogen, sulfur, silicon, phosphorus, boron, and the like either may or may not be present in the alkyl group), typically with from 1 to about 50 carbon atoms, or from about 1 to about 20 carbon atoms, and or from about 1 to about 10 carbon atoms, although the number of carbon atoms can be outside of these ranges, an aryl group (including substituted aryl groups, and wherein hetero atoms, such as oxygen, nitrogen, sulfur, silicon, phosphorus, boron, and the like either may or may not be present in the aryl group), typically with from about 6 to about 50 carbon atoms, or about 6 to about 20 carbon atoms, or about 6 to about 14 carbon atoms, although the number of carbon atoms can be outside of these ranges, an arylalkyl group (including substituted arylalkyl groups, and wherein hetero atoms, such as oxygen, nitrogen, sulfur, silicon, phosphorus, boron, and the like either may or may not be present in the aryl portion or the alkyl portion of the arylalkyl group), typically with from about 7 to about 50 carbon atoms, or about 7 to about 25 carbon atoms, or about 7 to about 15 carbon atoms, although the number of carbon atoms can be outside of these ranges, an alkylaryl group (including substituted alkylaryl groups, and wherein hetero atoms, such as oxygen, nitrogen, sulfur, silicon, phosphorus, boron, and the like either may or may not be present in the alkyl portion or the aryl portion of the alkylaryl group), or about 7 to about 50 carbon atoms, or about 7 to about 25 carbon atoms, or about 7 to about 15 carbon atoms, although the number of carbon atoms can be outside of these ranges, an alkoxy group (including linear, branched, saturated, unsaturated, cyclic, unsubstituted, and substituted alkoxy groups, and wherein hetero atoms, such as oxygen, nitrogen, sulfur, silicon, phosphorus, boron, and the like either may or may not be present in the alkyl portion of the alkoxy group), typically with from about 1 to about 50 carbon atoms, or about 4 to about 20 carbon atoms, or about 8 to about 12 carbon atoms, although the number of carbon atoms can be outside of these ranges, an aryloxy group (including substituted aryloxy groups, and wherein hetero atoms, such as oxygen, nitrogen, sulfur, silicon, phosphorus, boron, and the like either may or may not be present in the aryl portion of the aryloxy group), typically with from about 6 to about 50 carbon atoms, or about 6 to about 20 carbon atoms, or about 6 to about 14 carbon atoms, although the number of carbon atoms can be outside of these ranges, an arylalkyloxy group (including substituted arylalkyloxy groups, and wherein hetero atoms, such as oxygen, nitrogen, sulfur, silicon, phosphorus, boron, and the like either may or may not be present in the aryl portion or the alkyl portion of the arylalkyloxy group), typically with from about 7 to about 50 carbon atoms, or about 7 to about 25 carbon atoms, or about 7 to about 15 carbon atoms, although the number of carbon atoms can be outside of these ranges, an alkylaryloxy group (including substituted alkylaryloxy groups, and wherein hetero atoms, such as oxygen, nitrogen, sulfur, silicon, phosphorus, boron, and the like either may or may not be present in the alkyl portion or the aryl portion of the alkylaryloxy group), typically with from about 7 to about 50 carbon atoms, or about 7 to about 25 carbon atoms, or about 7 to about 15 carbon atoms, although the number of carbon atoms can be outside of these ranges, a polyalkyleneoxy group, wherein the alkyl portion of the repeat alkyleneoxy groups typically has from about 1 to about 12 carbon atoms, although the number of carbon atoms can be outside of these ranges, such as a polyethyleneoxy group, a polypropyleneoxy group, a polybutyleneoxy group, or the like, and wherein the number of repeat alkyleneoxy groups typically is from about 2 to about 50 repeat alkyleneoxy groups, although the number of repeat units can be outside of these ranges, a polyaryleneoxy group, wherein the aryl portion of the repeat aryleneoxy groups typically has from about 6 to about 14 carbon atoms, although the number of carbon atoms can be outside of these ranges, such as a polyphenyleneoxy group, a polynaphthaleneoxy group, a polyphenanthreneoxy group, or the like, and wherein the number of repeat aryleneoxy groups typically is from about 2 to about 20 repeat aryleneoxy groups, although the number of repeat units can be outside of these ranges, a polyarylalkyleneoxy group, wherein the arylalkyl portion of the repeat arylalkyleneoxy groups typically has from about 7 to about 50 carbon atoms, although the number of carbon atoms can be outside of these ranges, such as a polybenzyleneoxy group, a polyphenylethyleneoxy group, or the like, and wherein the number of repeat arylalkyleneoxy groups typically is from about 2 to about 20 repeat arylalkyleneoxy groups, although the number of repeat units can be outside of these ranges, a polyalkylaryleneoxy group, wherein the alkylaryl portion of the repeat alkylaryleneoxy groups typically has from about 7 to about 50 carbon atoms, although the number of carbon atoms can be outside of these ranges, such as a polytolueneoxy group or the like, and wherein the number of repeat alkylaryleneoxy groups typically is from about 2 to about 20 repeat alkylaryleneoxy groups, although the number of repeat units can be outside of these ranges, a heterocyclic group (including unsubstituted and substituted heterocyclic groups), typically with from about 2 to about 12 carbon atoms, and typically with from about 4 to about 18 ring atoms, although the number of carbon atoms and the number of ring atoms can be outside of these ranges, wherein the heteroatoms in the heterocyclic groups can be (but are not limited to) nitrogen, oxygen, sulfur, silicon, phosphorus, boron, and the like, as well as mixtures thereof, a silyl group (including unsubstituted and substituted silyl groups), a siloxane group (including unsubstituted and substituted siloxane groups), a polysilylene group (including unsubstituted and substituted polysilylene groups), typically with from 2 to about 100 repeat silylene units, or a polysiloxane group (including unsubstituted and substituted polysiloxane groups), typically with from 2 to about 200 repeat siloxane units, although the number of repeat siloxane units can be outside of this range, or (x) a phosphoryl group of the formula —PO$_3$R$_{90}$, wherein R$_{90}$ is a hydrogen atom, an alkyl group (including linear, branched, saturated, unsaturated, cyclic, unsubstituted, and substituted alkyl groups, and wherein hetero atoms, such as oxygen, nitrogen, sulfur, silicon, phosphorus, boron, and the like either may or may not be present in the alkyl group), typically with from 1 to about 50 carbon atoms, or about 1 to about 20 carbon atoms, or about 1 to about 10 carbon atoms, although the number of carbon atoms can be outside of these ranges, an aryl group (including substituted aryl groups), typically with from about 6 to about 50 carbon atoms, or about 6 to about 20 carbon atoms, or about 6 to about 14 carbon atoms, although the number of carbon atoms can be outside of these ranges, an arylalkyl group (including substituted arylalkyl groups), typically with from about 7 to about 50 carbon atoms, or about 7 to about 25 carbon atoms, or about 7 to about 15 carbon atoms, although the number of carbon atoms can be outside of these ranges, an alkylaryl group (including substituted alkylaryl groups), typically with from about 7 to about 15 carbon atoms, or about 7 to about 25 carbon atoms, or about 7 to about 15 carbon atoms, although the number of carbon atoms can be outside of these ranges, an alkoxy group (including linear, branched, saturated, unsaturated, cyclic, unsubstituted, and substituted alkoxy groups, and wherein hetero atoms, such as oxygen, nitrogen, sulfur, silicon, phosphorus, boron and the like either may or may not be present in the alkyl portion of the alkoxy group), typically with from about 1 to about 50 carbon atoms, or about 4 to about 20 carbon atoms, or about 8 to about 12 carbon atoms, although the number of carbon atoms can be outside of these ranges, an aryloxy group (including substituted aryloxy groups), typically with from about 6 to about 50 carbon atoms, or about 6 to about 20 carbon atoms, or about 6 to about 14 carbon atoms, although the number of carbon atoms can be outside of these ranges, an arylalkyloxy group (including substituted arylalkyloxy groups), typically with from about 7 to about 50 carbon atoms, or about 7 to about 25 carbon atoms, or about 7 to about 15 carbon atoms, although the number of carbon atoms can be outside of these ranges, an alkylaryloxy group (including substituted alkylaryloxy groups), typically with from about 7 to about 50 carbon atoms, or about 7 to about 25 carbon atoms, or about 7 to about 15 carbon atoms, although the number of carbon atoms can be outside of these ranges, a polyalkyleneoxy group, wherein the alkyl portion of the repeat alkyleneoxy groups typically has from about 1 to about 12 carbon atoms. although the number of carbon atoms can be outside of these ranges, such as a polyethyleneoxy group, a polypropyleneoxy group, a polybutyleneoxy group, or the like, and wherein the number of repeat alkyleneoxy groups typically is from about 2 to about 50 repeat alkyleneoxy groups, although the number of repeat units can be outside of these ranges, a polyaryleneoxy group, wherein the aryl portion of the repeat aryleneoxy groups typically has from about 6 to about 14 carbon atoms, although the number of carbon atoms can be outside of these ranges, such as a polyphenyleneoxy group, a polynaphthaleneoxy group, a polyphenanthreneoxy group, or the like, and wherein the number of repeat aryleneoxy groups typically is from about 2 to about 20 repeat aryleneoxy groups, although the number of repeat units can be outside of these ranges, a polyarylalkyleneoxy group, wherein the arylalkyl portion of the repeat arylalkyleneoxy groups typically has from about 7 to about 50 carbon atoms, although the number of carbon atoms can be outside of these ranges, such as a polybenzyleneoxy group, a polyphenylethyleneoxy group, or the like, and wherein the number of repeat arylalkyleneoxy groups typically is from about 2 to about 20 repeat arylalkyleneoxy groups, although the number of repeat units can be outside of these ranges, a polyalkylaryleneoxy group, wherein the alkylaryl portion of the repeat alkylaryleneoxy groups typically has from about 7 to about 50 carbon atoms, although the number of carbon atoms can be outside of these ranges, such as a polytolueneoxy group or the like, and wherein the number of repeat alkylaryleneoxy groups typically is from about 2 to about 20 repeat alkylaryleneoxy groups, although the number of repeat units can be outside of these ranges, a heterocyclic group (including unsubstituted and substituted heterocyclic groups), typically with from about 2 to about 12 carbon atoms, and typically with from about 4 to about 18 ring atoms, although the number of carbon atoms and the number of ring atoms can be outside of these ranges, wherein the heteroatom in the heterocyclic groups can be (but are not limited to) nitrogen, oxygen, sulfur, silicon, phosphorus, boron, and the like, as well as mixtures thereof, a silyl group (including unsubstituted and substituted silyl groups), a siloxane group (including unsubstituted and substituted siloxane groups), a polysilylene group (including unsubstituted and substituted polysilylene groups), typically with from 2 to about 100 repeat silylene units, or a polysiloxane group (including unsubstituted and substituted polysiloxane groups), typically with from 2 to about 200 repeat siloxane units, although the number of repeat siloxane units can be outside of this range, wherein the substituents on the substituted alkyl, aryl, arylalkyl, alkylaryl, alkoxy, aryloxy, arylalkyloxy, alkylaryloxy, polyalkyleneoxy, polyaryleneoxy, polyarylalkyleneoxy, polyalkylaryleneoxy, heterocyclic, silyl, siloxy, polysilylene, and polysiloxy groups are hydroxy groups, halogen atoms, cyano groups, ether groups, aldehyde groups, ketone groups, carboxylic acid groups, ester groups, amide groups, carbonyl groups, thiocarbonyl groups, sulfate groups, sulfonate groups, sulfide groups, sulfoxide groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like, wherein the substituents on the silylene, siloxy, polysilylene, and polysiloxy groups can also be alkyl groups, aryl groups, arylalkyl groups, and alkylaryl groups, wherein two or more substituents can be joined together to form a ring, and wherein Z and Z' can be the same as each other or different from each other. Up to 4 Z groups can be present on the molecule. Up to 4 Z' groups can be present on the molecule.

The groups Z and X can be joined together to form a ring and the groups Z' and X' can be joined together to form a ring.

For example, in embodiments wherein X or X and X' is oxygen, compounds disclosed herein include but are not limited to compounds of the formula

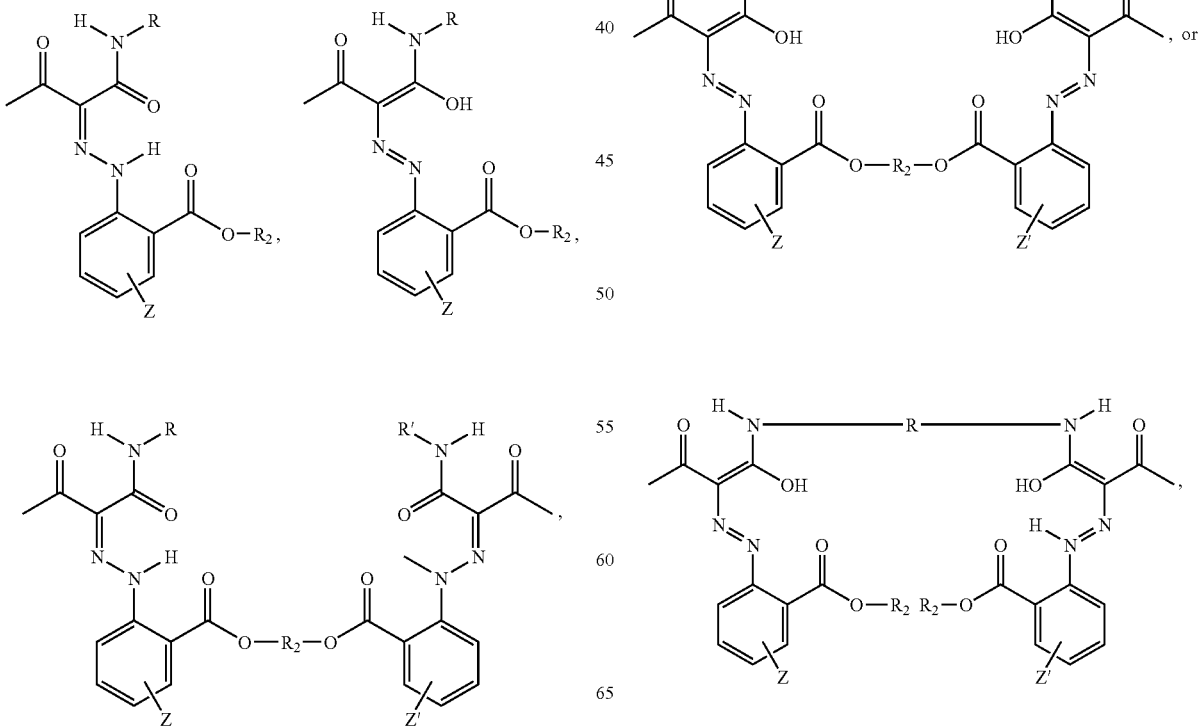

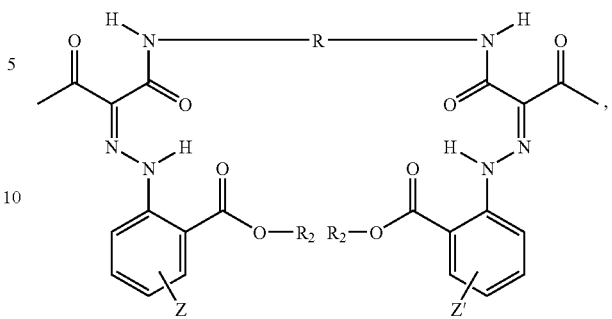

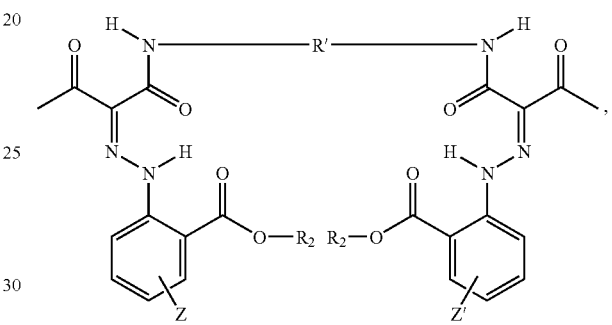

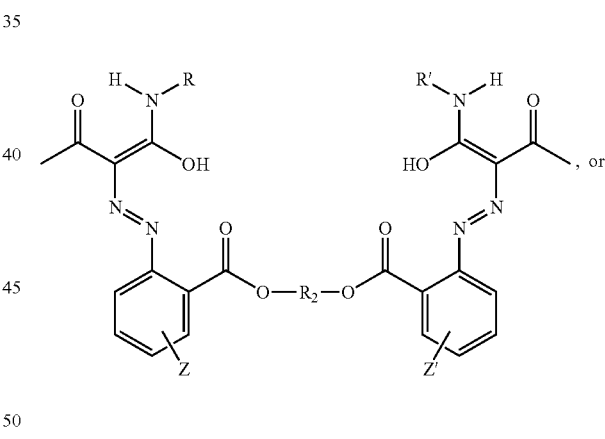

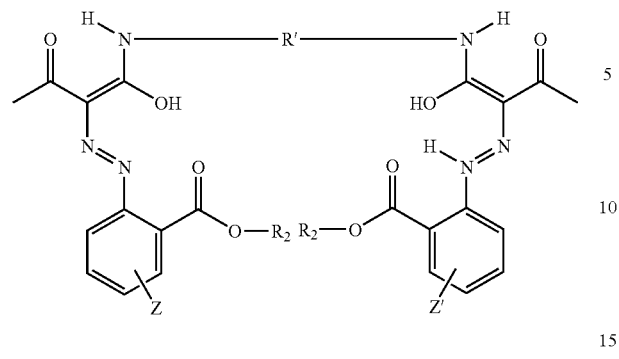
Some specific examples include, but are not limited to,
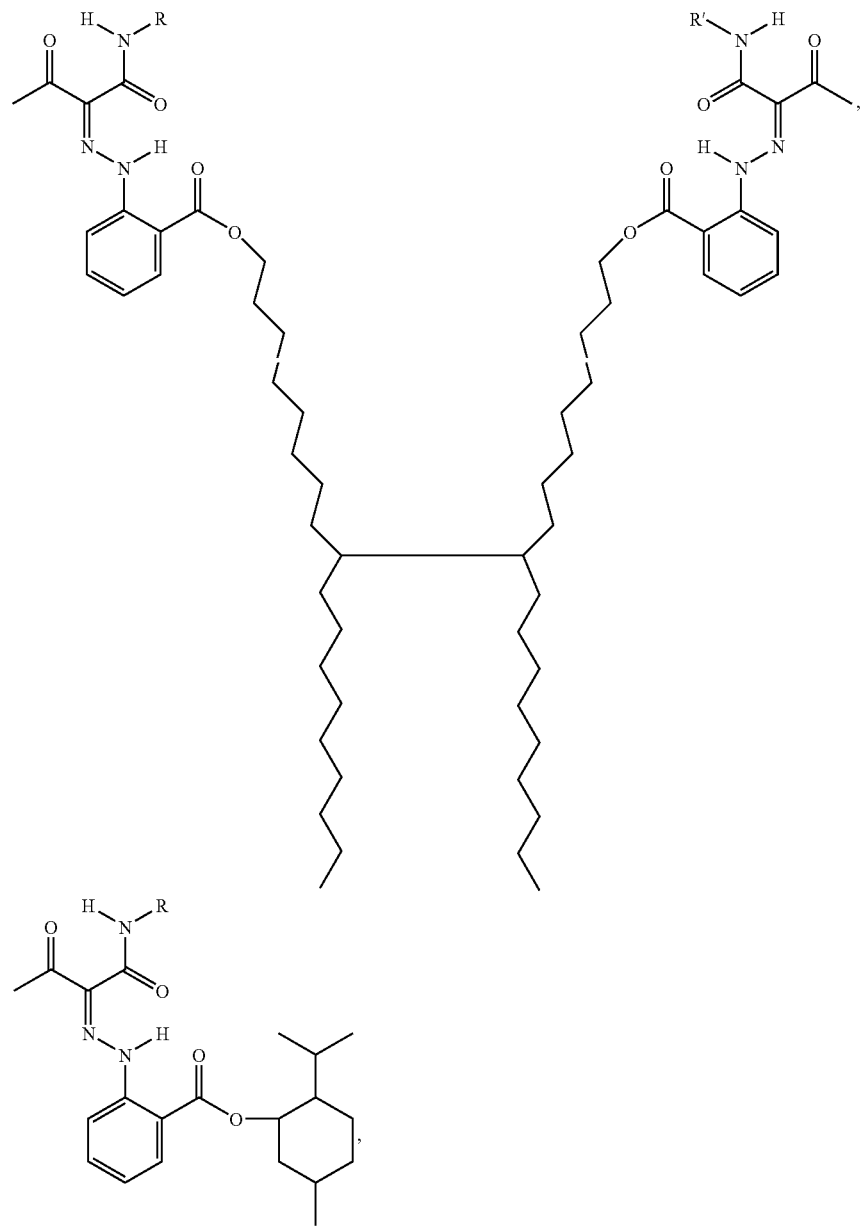
wherein R, R' is an N-substituted acetoacetamide;

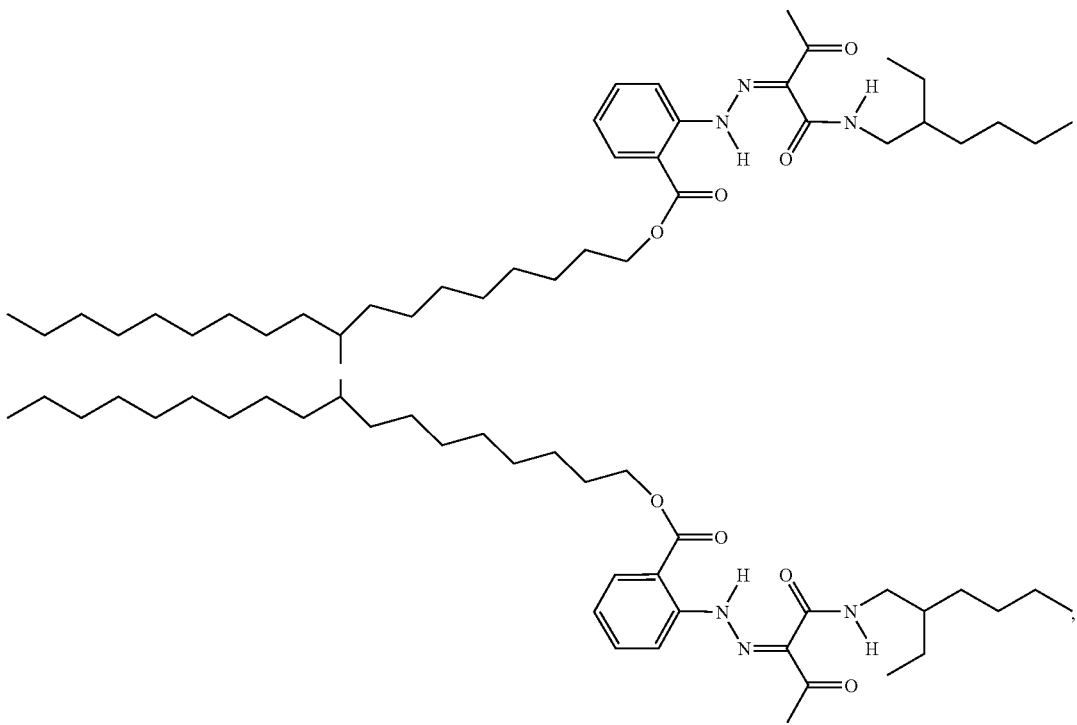
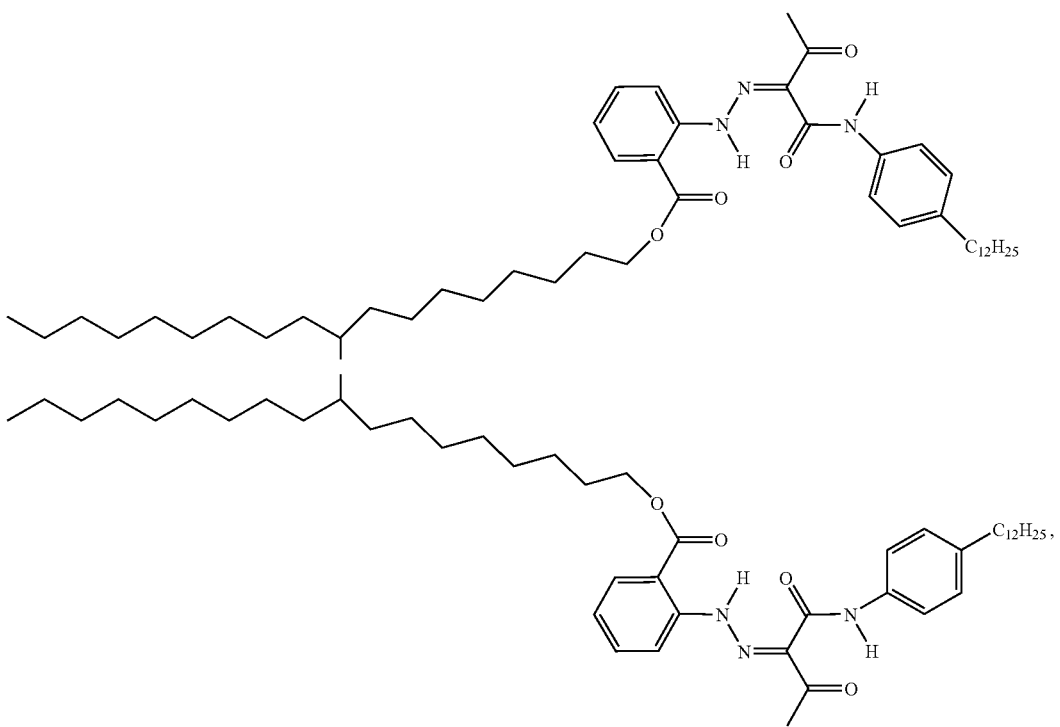

-continued
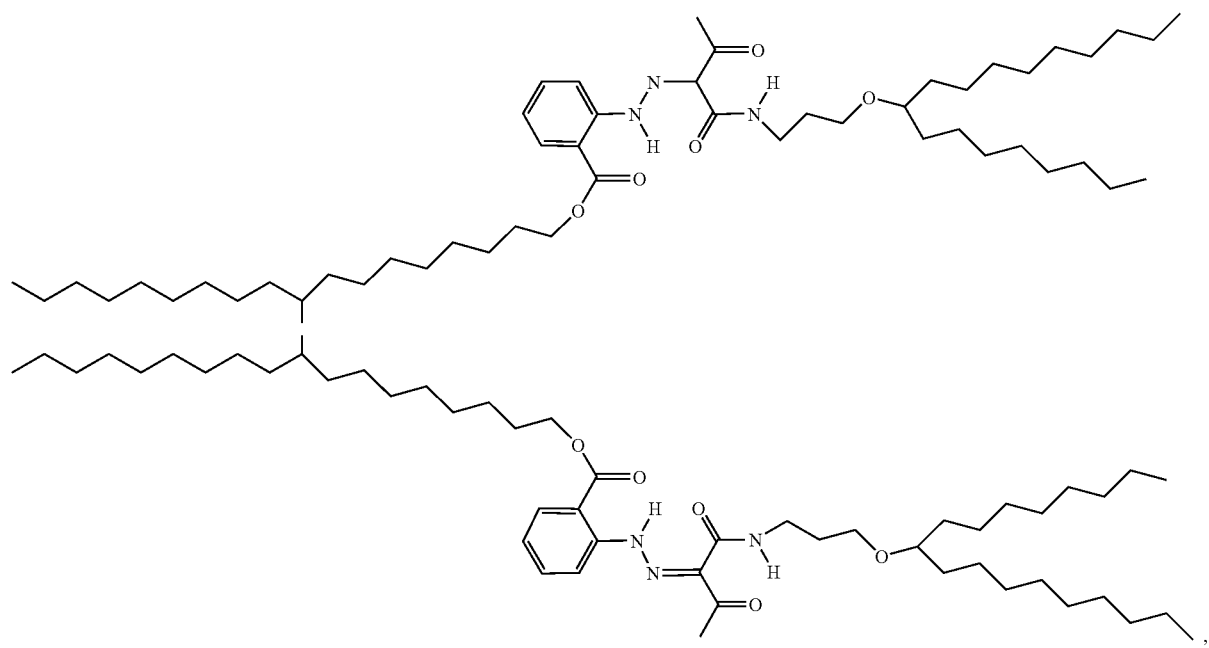
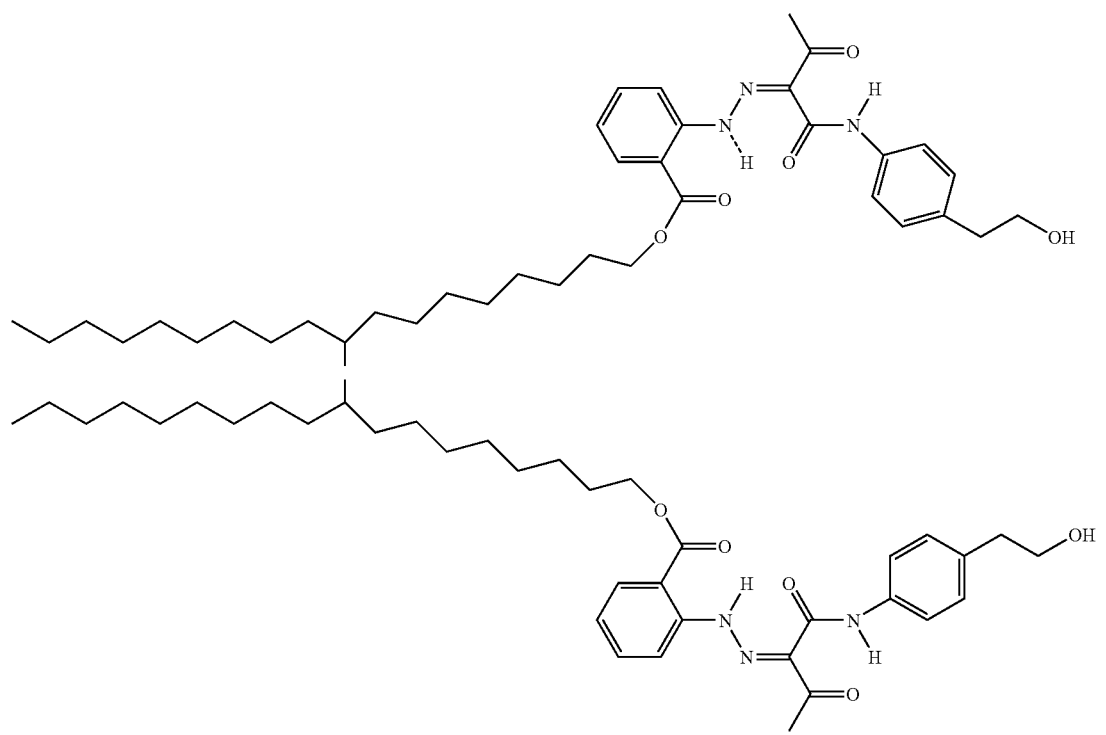

-continued

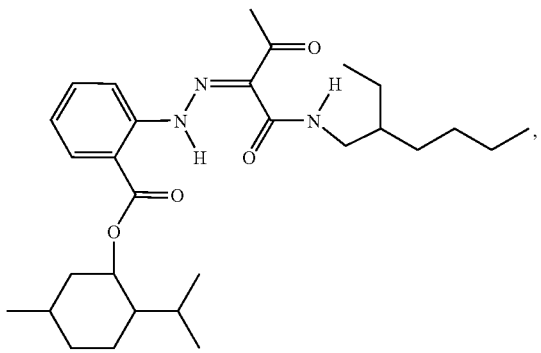, 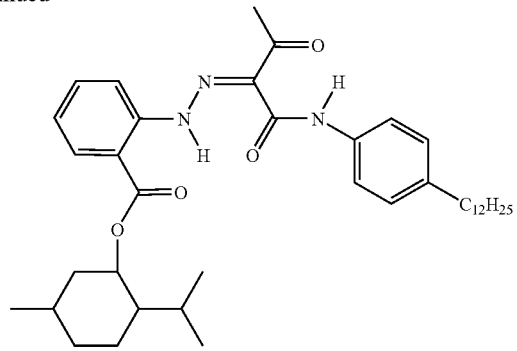

and the like.

Colorants of the present disclosure can be prepared by any desired or effective procedure. For example, they can be prepared by diazotization of the correspondingly substituted dimeric anthranilate compound with nitrosylsulfuric acid under cold temperature conditions, followed by coupling with the correspondingly substituted acetoacetamido in a buffered alkaline aqueous solution under cold temperature conditions, as follows:

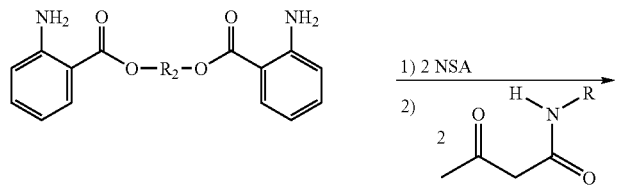 → 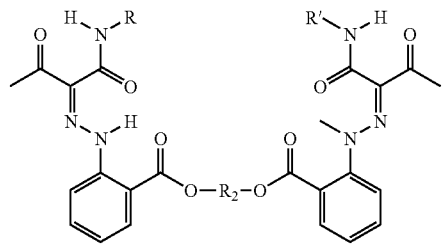

Other methods can be employed including use of $KNO_2$ or $NaNO_2$ and a mineral acid such a HCl or $H_2SO_4$. More specifically, the correspondingly substituted dianthranilate is first subjected to a diazotization reaction by dissolving it in acetic acid diluted with a solvent and, optionally, a second acid, such as sulfuric acid, dodecylbenzene sulfonic acid, propionic acid, hydrochloric acid, phosphoric, acid, and other acid useful for a diazotization reaction, or the like, as well as mixtures thereof. The solvent can be any solvent useful in a diazotization reaction, such as water, acetone, dimethylformamide, dimethyacetamide, tetrahydrofuran, dimethoxyethane, analogous higher-boiling ether solvents, and the like, as well as mixtures thereof.

The solvent and the dianthranilate are present in any desired or effective relative amounts; if, for purposes of determining relative amounts, "solvent" is defined to include whatever solvent has been selected plus any amount of acetic acid and second acid present, the reactants are present in this combined solvent in relative amounts of in one embodiment at least about 100 grams of substituted dianthranilate per liter of solvent, in another embodiment at least about 200 grams of substituted dianthranilate per liter of solvent, and in yet another embodiment at least about 230 grams of substituted dianthranilate per liter of solvent, and in one embodiment of no more than about 400 grams of substituted dianthranilate per liter of solvent, in another embodiment of no more than about 300 grams of substituted dianthranilate per liter of solvent, and in yet another embodiment of no more than about 270 grams of substituted dianthranilate per liter of solvent, although the relative amounts can be outside of these ranges.

The acetic acid is present in any desired or effective amount, in one embodiment at least about 1 gram of acetic acid per gram of substituted dianthranilate, in another embodiment at least about 2 grams of acetic acid per gram of substituted dianthranilate, and in yet another embodiment at least about 3 grams of acetic acid per gram of substituted dianthranilate, and in one embodiment no more than about 10 grams of acetic acid per gram of substituted dianthranilate, in another embodiment no more than about 7 grams of acetic acid per gram of substituted dianthranilate, and in yet another embodiment no more than about 5 grams of acetic acid per gram of substituted dianthranilate, although the relative amounts can be outside of these ranges.

When present, the optional second acid is present in any desired or effective amount, in one embodiment at least about 0.05 gram of acid per gram of substituted dianthranilate, and in another embodiment at least about 0.1 gram of acid per gram of substituted dianthranilate, and in one embodiment no more than about 0.5 grams of acid per gram of substituted dianthranilate, in another embodiment no more than about 0.3 grams of acid per gram of substituted dianthranilate, and in yet another embodiment no more than about 0.2 grams of acid per gram of substituted dianthranilate, although the relative amounts can be outside of these ranges.

In the mixture comprising the selected solvent, any optional second acid, and acetic acid, the acetic acid is present in any desired or effective amount, in one embodiment at least about 50 percent by volume of the mixture, in another embodiment at least about 70 percent by volume of the mixture, in yet another embodiment at least about 75 percent by volume of the mixture, and in still another embodiment at least about 95 percent by volume of the mixture, although the relative amount can be outside of these ranges.

Upon complete dissolution of the ingredients, the mixture is cooled, in one embodiment to a temperature of no more than about +15° C., in another embodiment to a temperature of no more than about +10° C., in yet another embodiment to a temperature of no more than about +5° C., in still another embodiment to a temperature of no more than about +3° C., and in one embodiment to a temperature of no lower than about −5° C., and in another embodiment to a temperature of no lower than about −10° C., although the temperature can be outside of these ranges.

Thereafter, nitrosylsulfuric acid, or other acid if other method is employed, is added to the mixture in any desired or effective amount, in one embodiment at least about 2 moles of nitrosylsulfuric acid per mole of substituted dianthranilate (i.e., at least about 1 mole of nitrosylsulfuric acid per mole of aniline moiety in the dianthranilate), and in another embodiment at least about 2.1 moles of nitrosylsulfuric acid per mole of substituted dianthranilate, and in one embodiment no more than about 3 moles of nitrosylsulfuric acid per mole of substituted dianthranilate, in another embodiment no more than about 2.5 moles of nitrosylsulfuric acid per mole of substituted dianthranilate, and in yet another embodiment no more than about 2.25 moles of nitrosylsulfuric acid per mole of substituted dianthranilate, although the relative amounts can be outside of these ranges. In a specific embodiment the nitrosylsulfuric acid is added dropwise at a rate such that the temperature of the reaction mixture does not exceed 15° C.

The reaction to form the diazonium salt is essentially instantaneous, and upon completion of addition of the nitrosylsulfuric acid the reaction is essentially complete. At times, the reaction can take a period of time to complete, from instantaneous to about 6 hours. If desired, a qualitative test can be performed to confirm reaction completion.

Thereafter, residual excess nitrosylsulfuric acid present in the reaction mixture can be quenched by the addition of a quenching agent, such as sulfamic acid, urea, or the like as well as mixtures thereof, in any desired or effective amount, in one embodiment at least about 0.01 mole of quenching agent per mole of nitrosylsulfuric acid (i.e., per mole of nitrosylsulfuric acid originally added to the reaction mixture), in another embodiment at least about 0.05 mole of quenching agent per mole of nitrosylsulfuric acid, and in yet another embodiment at least about 0.1 mole of quenching agent per mole of nitrosylsulfuric acid, and in one embodiment no more than about 0.5 mole of quenching agent per mole of nitrosylsulfuric acid, in another embodiment no more than about 0.3 mole of quenching agent per mole of nitrosylsulfuric acid, and in yet another embodiment no more than about 0.2 mole of quenching agent per mole of nitrosylsulfuric acid, although the amount can be outside of these ranges. Upon completion of the reaction, the reaction mixture contains the corresponding diazonium salt.

A precursor solution of the acetoacetamide having the desired substituents thereon is prepared neat, or in an appropriate solvent, such as a mixture of water, organic solvents, including lower alcohols such as methanol, ethanol, isopropanol, and the like, water-miscible nonbasic organic solvents such as tetrahydrofuran, acetone, dimethoxyethane, N,N-dimethylformamide, N,N-dimethylacetamide, acetonitrile, and the like, as well as mixtures thereof. Mixtures of water with an organic solvent can be helpful for ease of solvating inorganic or organic salts that are a reaction by-product. In this instance, water and the organic solvent are present in any desired or effective relative amounts, in one embodiment at least about 0.25 gram of organic solvent per gram of water, in another embodiment at least about 0.3 gram of organic solvent per gram of water, and in yet another embodiment at least about 0.4 gram of organic solvent per gram of water, and in one embodiment no more than about 4 grams of organic solvent per gram of water, in another embodiment no more than about 3 grams of organic solvent per gram of water, and in yet another embodiment no more than about 2 grams of organic solvent per gram of water, although the relative amounts can be outside of these ranges.

The acetoacetamide is present in the precursor solution in any desired or effective amount, in one embodiment at least about 10 grams of acetoacetamide per liter of solvent, in another embodiment at least about 30 grams of acetoacetamide per liter of solvent, and in yet another embodiment at least about 50 grams of acetoacetamide per liter of solvent, and in one embodiment no more than about 200 grams of acetoacetamide per liter of solvent, in another embodiment no more than about 100 grams of acetoacetamide per liter of solvent, and in yet another embodiment no more than about 70 grams of acetoacetamide per liter of solvent, although the relative amounts can be outside of these ranges.

The acetoacetamide precursor solution is prepared, the acetonitrile is distilled off, and the product is stored in a jar. It doesn't say that the product is stored in an alkaline solution. If desired, the acetoacetamide precursor solution can be maintained at an alkaline pH, typically of at least about 10, and in one embodiment no more than about 14, and in another embodiment no more than about 12, although the pH can be outside of these ranges. The acetoacetamide precursor solution can contain a mixture of a base and an optional buffering salt.

Examples of suitable bases include mineral bases, such as sodium hydroxide, potassium hydroxide, and the like, as well as water-miscible organic tertiary amines, such as triethanolamine, N,N-diethylethanolamine, and the like, as well as mixtures thereof, present in any desired or effective amount, in one embodiment at least about 1 mole of base per mole of acetoacetamide, in another embodiment at least about 2 moles of base per mole of acetoacetamide, in yet another embodiment at least about 3 moles of base per mole of acetoacetamide, and in still another embodiment at least about 5 moles of base per mole of acetoacetamide, and in one embodiment no more than about 10 moles of base per mole of acetoacetamide, in another embodiment no more than about 7 moles of base per mole of acetoacetamide, and in yet another embodiment no more than about 5 moles of base per mole of acetoacetamide, although the relative amounts can be outside of these ranges.

Examples of suitable optional buffer salts include those corresponding to the principal acid solvent; for example, when the principal acid solvent is acetic acid, suitable buffers include sodium acetate, potassium acetate, sodium hydrogenphosphate, citric acid, and the like, as well as mixtures thereof. When present, the optional buffer salt is present in any desired or effective amount, in one embodiment at least about 1 mole of buffer per mole of acetoacetamide, in another embodiment at least about 2 moles of buffer per mole of acetoacetamide, in yet another embodiment at least about 3 moles of buffer per mole of acetoacetamide, and in still another embodiment at least about 5 moles of buffer per mole of acetoacetamide, and in one embodiment no more than about 10 moles of buffer per mole of acetoacetamide, in another embodiment no more than about 7 moles of buffer per mole of acetoacetamide, and in yet another embodiment no more than about 5 moles of buffer per mole of acetoacetamide, although relative amounts can be outside of these ranges. In a specific embodiment, upon dissolution of the acetoacetamide, the thus-formed precursor acetoacetamide solution can be filtered to remove any undissolved solids.

The solution containing the diazonium salt, maintained at a cold temperature, is then slowly added to the acetoacetamide solution in any desired or effective relative amounts. If the diazonium salt is of a dimeric species (that is, a bis-diazonium salt), in one embodiment at least about 2 moles of acetoacetamide per mole of diazonium salt, in another embodiment at least about 2.1 moles of acetoacetamide per mole of diazonium salt, and in yet another embodiment at least about 2.25 moles of acetoacetamide per mole of diazonium salt, and in one embodiment no more than about 4 moles of acetoacetamide per mole of diazonium salt, in another embodiment no more than about 3 moles of acetoacetamide per mole of diazonium salt, and in yet another embodiment no more than about 2.5 moles of acetoacetamide per mole of diazonium salt, if a monomeric diazonium salt is selected, the moles of acetoacetamide should be halved, although the relative amounts can be outside of these ranges, resulting in the immediate formation of a bright yellow precipitate. Thereafter, the yellow precipitate can be collected by filtration and, if desired, washed.

In embodiments, a reaction scheme herein includes, for example,

Chemical Reviews, 1986, Vol. 86, No. 2, pp. 241-258, by Robert Clemens, the disclosure of which is totally incorporated herein by reference.

While not being limited to any particular theory, it is believed that in embodiments the structure of the present compounds provide improved migratory and diffusion properties. Further, while not being limited to any particular theory, it is believed that in embodiments the waxy appendages (that is, long chains) protruding from the chromophore at each end provide a compound that is compatible and soluble in the phase change ink base. It is believe that this structural feature can also impart thermal stability and chemical stability to the colorant molecule. Further, while not being limited to any particular theory, it is believed that including alkyl or alkylene groups with at least about 12 carbon atoms, particularly (although not necessarily) branched alkyl groups of this type, in the colorant molecule further reduce diffusion or leaching of the colorant molecule from a medium such as a phase change ink vehicle into adjacent inks of different colors (leading to intercolor bleed), adjacent unprinted areas (leading to edge raggedness), tape adhesives (leading to edge raggedness and possible illegibility), and the like.

In addition to being suitable for use in phase change inks, the colorants of the present disclosure can be used in applications such as textile dyeing, biological dyeing applications that rely on high spectral strength chromophores, electronics applications, such as organic photoconductors, optical filters, and the like, color filters for liquid crystal display systems, and the like.

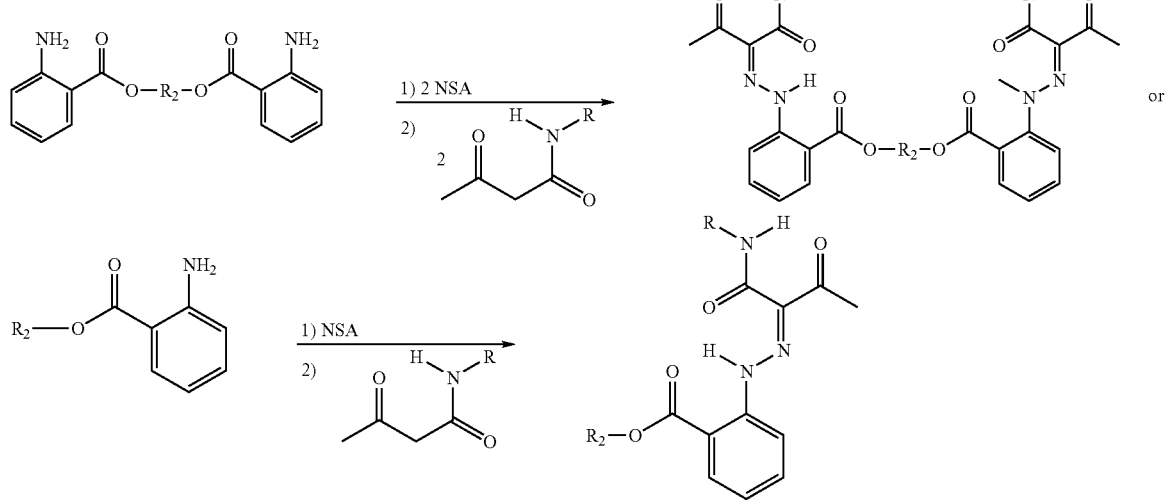

Precursor dianthranilates can be prepared by any desired or effective method, such as that disclosed in, for example, U.S. Pat. No. 6,713,614 and U.S. Pat. No. 6,576,747, the disclosures of each of which are totally incorporated herein by reference.

Precursor acetoacetamides can be prepared by any desired or effective method, such as that disclosed in, for example,

EXAMPLES

The following Examples are being submitted to further define various species of the present disclosure. These Examples are intended to be illustrative only and are not intended to limit the scope of the present disclosure. Also, parts and percentages are by weight unless otherwise indicated.

Example 1

Synthesis of 2-ethylhexylacetoacetamide

An acetoacetamide compound of the formula

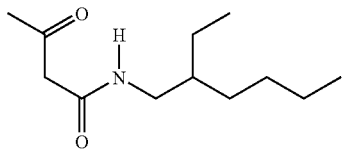

was prepared as follows,

Into a 250 milliliter 3-neck round bottom flask equipped with a magnetic stirrer, a silicone oil bath and a condenser was charged 38.4 grams of 2-ethylhexylamine (MW=129) and about 100 grams of acetonitrile. With stirring at room temperature, about 25.0 grams of diketene (MW=84) was added. An exotherm was observed. The round bottom flask was put in an 80° C. oil bath and refluxed for about 3 hours. The acetonitrile was distilled off and the temperature of the reaction increased to 120° C. for about 2 hrs. The product was poured into a jar.

Example 2

Synthesis of Dodecylanilineacetoacetamide

An acetoacetamide compound of the formula

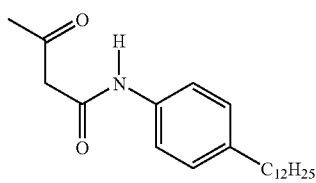

was prepared as follows:

To a 500 milliliter 3-neck round bottom flask equipped with magnetic stirrer, a silicone oil bath and a condenser was charged about 77.7 grams of dodecylaniline (MW=261, available from EMF-Dottikon), about 25.0 grams of diketene (MW=84) and about 150 grams of acetonitrile. With stirring at room temperature, about 25.0 grams of diketene (MW=84) was added. An exotherm was observed. The round bottom flask was put in an 80° C. oil bath and refluxed for about 3 hours. The acetonitrile was distilled off and the temperature of the reaction increased to about 120° C. for about 2 hours. The product was poured into a jar.

Example 3

Synthesis of Guerbet-acetoacetamide

An acetoacetamide compound of the formula

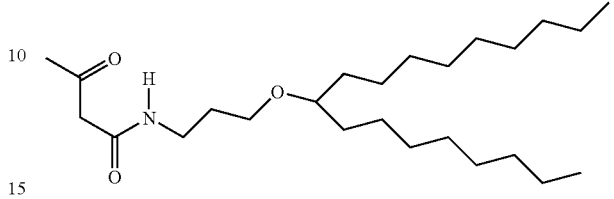

was prepared as follows.

To a 250 milliliter 3-neck round bottom flask equipped with magnetic stirrer, a silicon oil bath and a condenser was charged about 42.3 grams of PA-24 (MW=355 Guerbet amine available from the Tomah Chemical Co.) and about 75 grams of acetonitrile. The two chemicals were not miscible. When about 10.0 grams of diketene (MW=84) was added, an exotherm was observed and all chemicals became miscible. The round bottom flask was placed in an about 80° C. oil bath and refluxed for about 1 hour. The acetonitrile was distilled off and the temperature of the reaction increased to about 120° C. for about 1 hours. The product was poured into a jar.

Example 4

Synthesis of p-hydroxyethylanilino-acetoacetamide

An acetoacetamide compound of the formula

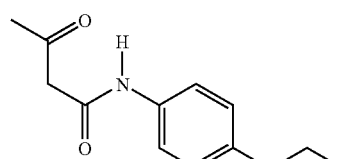

was prepared as follows.

To a 100 milliliter 3-neck round bottom flask equipped with magnetic stirrer, a silicone oil bath and a condenser was charged about 16.3 grams 4-aminophenethyl alcohol (available from Aceto Corporation, MW=137) and about 75 grams of acetonitrile. It did not totally dissolve. About 10.0 grams of diketene (MW=84) was added. The round bottom flask was placed in an about 80° C. oil bath and refluxed for about 1 hour. All dissolved. The acetonitrile was distilled off and the temperature of the reaction increased to about 120° C. for about 2 hours. The product was poured into a jar.

Example 5

Synthesis of Dimer Dianthranilate Bis-(2-ethylhexylacetoacetamide) Azo

Part A: Dimer Dianthranilate Bis-Diazotization

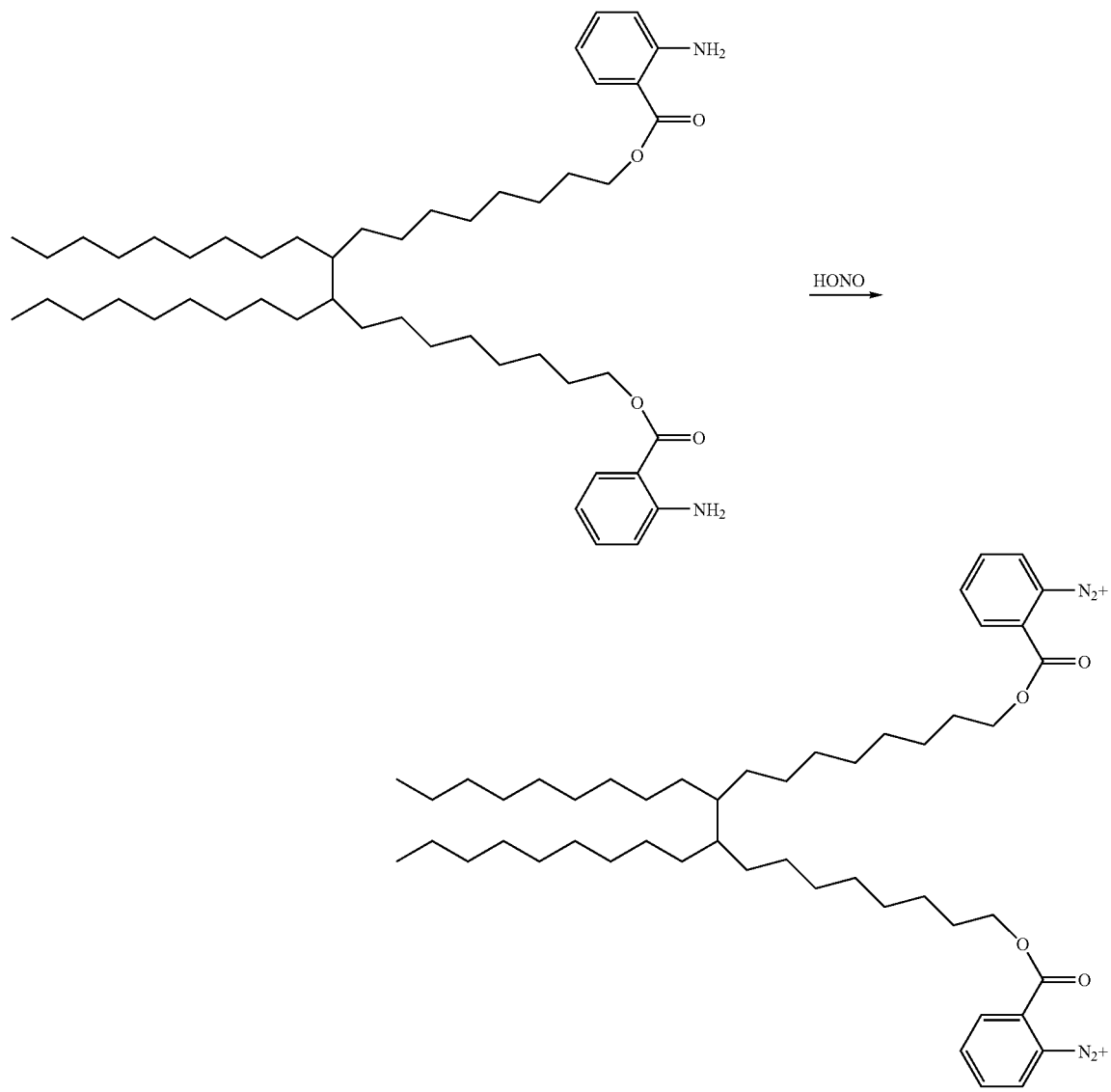

To a 1 liter 3-neck round bottom flask equipped with mechanical stirrer, a silicone oil bath and a thermometer was charged about 21.6 grams (MW=776) of dimer ester anthranilate (DEA) precursor (the preparation of which is found in Example 1 of U.S. Pat. No. 6,713,614, the disclosure of which is hereby incorporated by reference herein in its entirety) followed sequentially with about 42 milliliters of glacial acetic acid, about 3.6 milliliters of concentrated sulfuric acid, about 4.0 milliliters of deionized water and about 4.4 milliliters of propionic acid. All dissolved. The round bottom flask was put in an ice bath and stirred until the temperature was about 3° C. to about 5° C. To a constant pressure addition funnel was charged about 11.2 milliliters (0.057 moles) of nitrosyl sulfuric acid (NSA, MW=127, 40% by weight in sulfuric acid). The NSA solution was added slowly into the brown DEA solution to maintain the reaction temperature between about 3° C. to about 10° C. After about 2 hours, the addition was complete and the contents were stirred for another half hour. A phosphomolybdic acid test (PMA test) was run to determine if the reaction was completed. The result was negative which suggested the reaction had not completed and more NSA was needed. About 1.0 g additional NSA was added. After about 15 minutes, a PMA test was run and the result was still negative. About 0.4 g NSA was added. After about 15 minutes, another PMA test was run and the result was negative. Another about 0.4 grams of NSA was added and another PMA test was run. This time the result was positive. Then about 0.6 gram of sulfamic acid was added to react with excess NSA. A PMA test was run after about 15 minutes and it indicated that all NSA was reacted. At this point the azo was ready to add to the coupler.

Example 5

Synthesis of Dimer Dianthranilate Bis-(2-ethylhexylacetoacetamide) Azo

Part B: The Coupling of Dimer Dianthranilate Bis-Diazo to 2-Ethylhexylacetoacetamide A compound of the formula

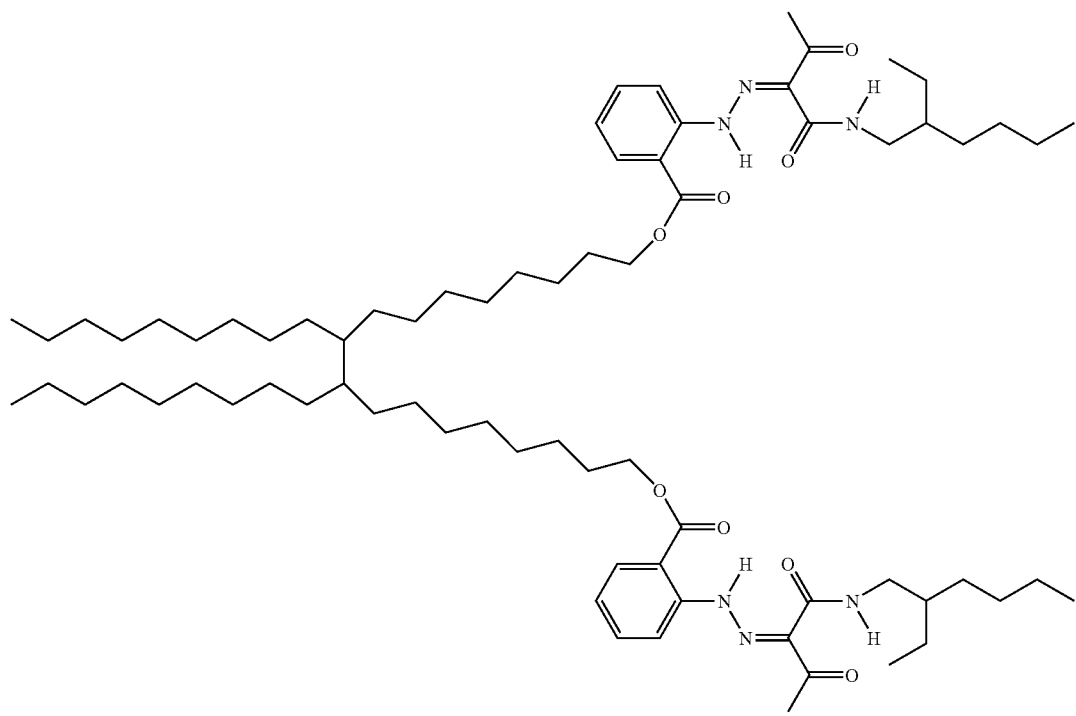

was prepared as follows.

Dissolving the 2-ethylhexylacetoacetamide. To a 2 liter beaker equipped with a magnetic stir bar was charged about 700 grams of deionized water, about 16.0 grams of acetic acid, and about 22.2 grams of sodium hydroxide. The contents were stirred until completely dissolved. About 700 milliliters of isopropyl alcohol and about 11.8 grams of 2-ethylhexylacetoacetamide from Example 1 above was then added and stirred until all was dissolved.

Adding the Dimer Dianthranilate Bis-Diazo to the Dissolved 2-ethylhexylacetoacetamide. The cooled contents from Example 5. Part A were slowly added to the beaker containing the 2-ethylhexylacetoacetamide solution. A yellowish liquid contained white salt and yellow product. About 700 milliliters of deionized water was added to the solids and stirred for about one hour. The aqueous layer was then discarded. The bottom yellow viscous liquid product was dissolved in about 300 milliliters of toluene and washed with water in a separatory funnel. The lower water layer was discarded and the top toluene layer was run through a silica plug. Then the toluene was evaporated yielding a viscous very dark yellow dye. The spectral strength of the yellow colorant was determined using a spectrophotometric procedure based on the measurement of the colorant in solution by dissolving the colorant in toluene and measuring the absorbance using a Perkin Elmer Lambda 2S UV/VIS spectrophotometer. The spectral strength of the colorant measured in toluene was about 35,330 mL* Absorbance Units per gram at absorption $\lambda_{max}$.

Example 6: The Coupling of Dimer Dianthranilate Bis-Diazo to dodecylanilineacetoacetamide A compound of the formula

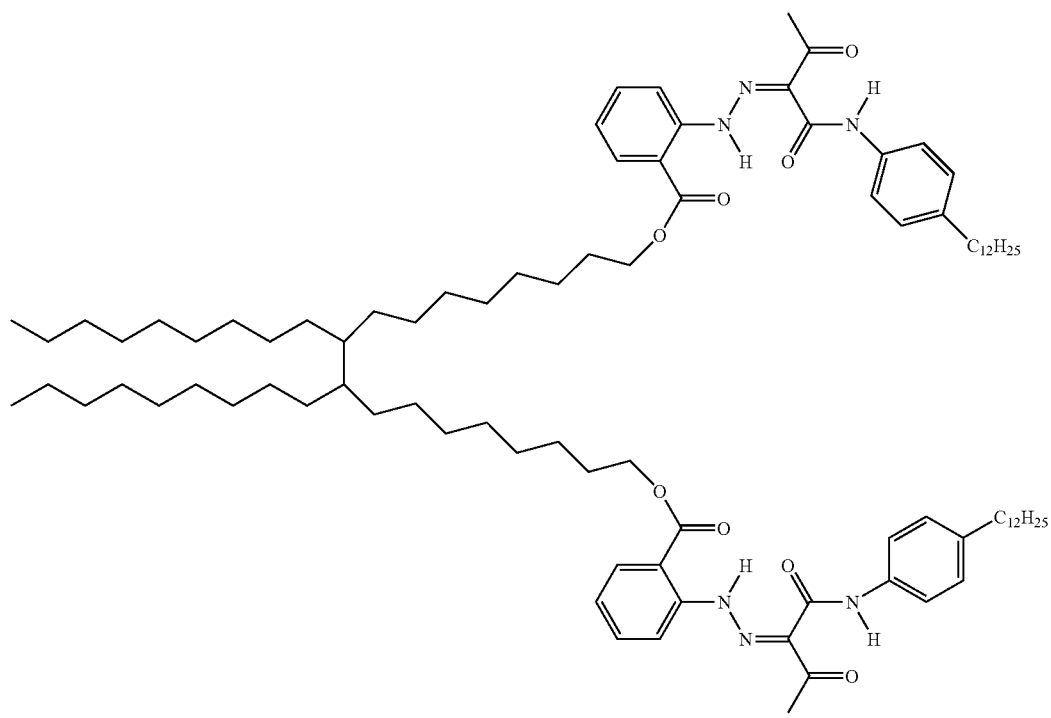

was prepared as follows.

Dissolving the dodecylanilineacetoacetamide: To a 4 liter beaker with magnetic stir bar was charged about 700 grams of deionized water, about 16.0 grams of acetic acid, and about 22.2 grams of sodium hydroxide. The contents were stirred until completely dissolved. About 1700 milliliters isopropyl alcohol and about 18.8 grams of dodecylanilineacetoacetamide from Example 2 above was then added and stirred until dissolved.

Adding the Dimer Dianthranilate Bis-Diazo to the Dissolved Dodecylanilino-acetoacetamide: The cooled contents from Example 5, Part A above were slowly added to the beaker containing the dodecylanilineacetoacetamide solution. A yellow precipitate formed at the beginning of coupling, and then the solids turned into a very viscous liquid. At the end of coupling two types of solids formed. One was yellow sticky solid while the other was a very fine solid. After stirring for about one hour the contents were allows to settle over night. The top liquid was decanted. The sticky solid was easily separated from the very fine solid which turned out to be salts and were removed by dissolving in water. The sticky yellow solid was dissolved in about 300 milliliters of toluene and washed with water in a separatory funnel. The lower water layer was discarded and the top toluene layer was run through a silica plug. Then the solvent was evaporated yielding a viscous very dark yellow dye. The special strength of the yellow colorant was determined using a spectrophotometric procedure based on the measurement of the colorant in solution by dissolving the colorant in toluene and measuring the absorbance using a Perkin Elmer Lambda 2S UV/VIS spectrophotometer. The spectral strength of the colorant measured in toluene as about 30,285 mL* Absorbance Units per gram at absorption $\lambda_{max}$.

Example 7: The Coupling of Dimer Dianthranilate Bis-Diazo to Guerbet-acetoacetamide A compound of the formula

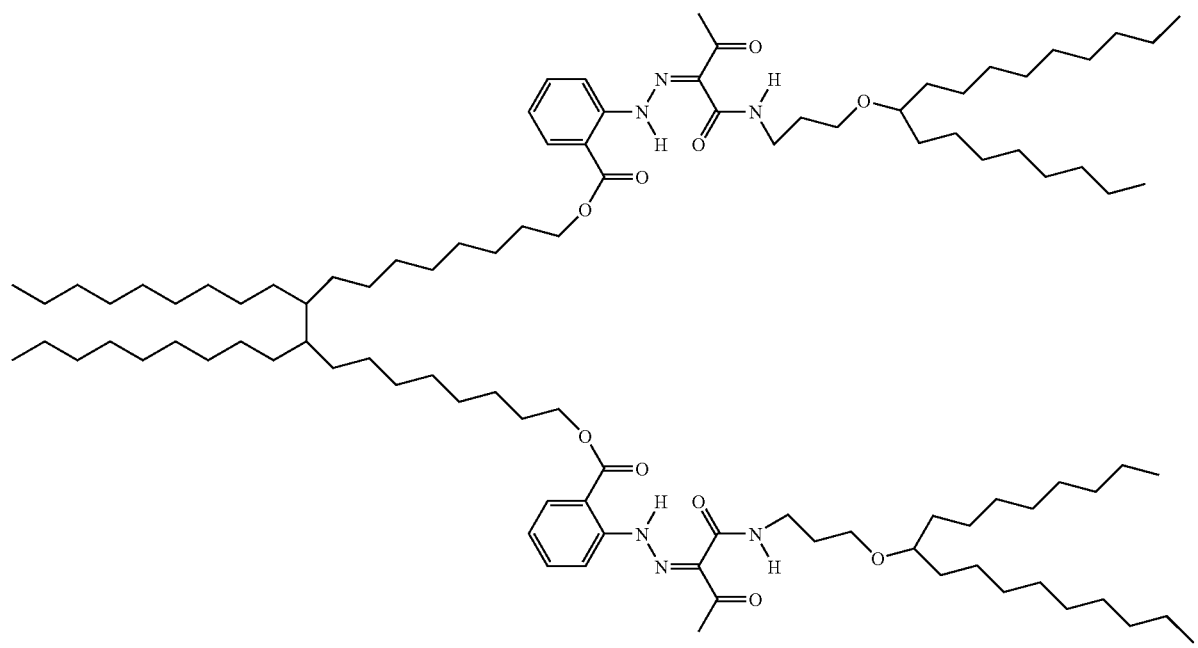

was prepared as follows.

Dissolving the Guerbet-acetoacetamide. To a 4 liter beaker with magnetic stir bar was charged about 700 grams of deionized water, about 16.0 grams of acetic acid, and about 22.2 grams of sodium hydroxide. The contents were stirred until completely dissolved. About 2300 milliliters isopropyl alcohol and about 24.0 grams of Guerbet-acetoacetamide from Example 3 above was then added and stirred until dissolved.

Adding the Dimer Dianthranilate Bis-Diazo to the Dissolved Guerbet-acetoacetamide: The cooled contents from Example 5, Part A above were slowly added to the beaker containing the Guerbet-acetoacetamide solution. A yellow precipitate formed at the beginning of coupling then the solids turned into a very viscous liquid. The precipitate was collected and dissolved in about 300 milliliters of toluene and washed with water in a separate funnel. The lower water layer was discarded and the top toluene layer was run through a silica plug. Then the solvent was evaporated yielding a viscous very dark yellow dye. The spectral strength of the yellow colorant was determined using a spectrophotometric procedure based on the measurement of the colorant in solution by dissolving the colorant in toluene and measuring the absorbance using a Perkin Elmer Lambda 2S UV/VIS spectrophotometer. The spectral strength of the colorant measured in toluene as about 27,194 mL* Absorbance Units per gram at absorption $\lambda_{max}$.

Example 8: The Coupling of Dimer Dianthranilate Bis-Diazo to p-hydroxyethylanilino-acetoacetamide A compound of the formula

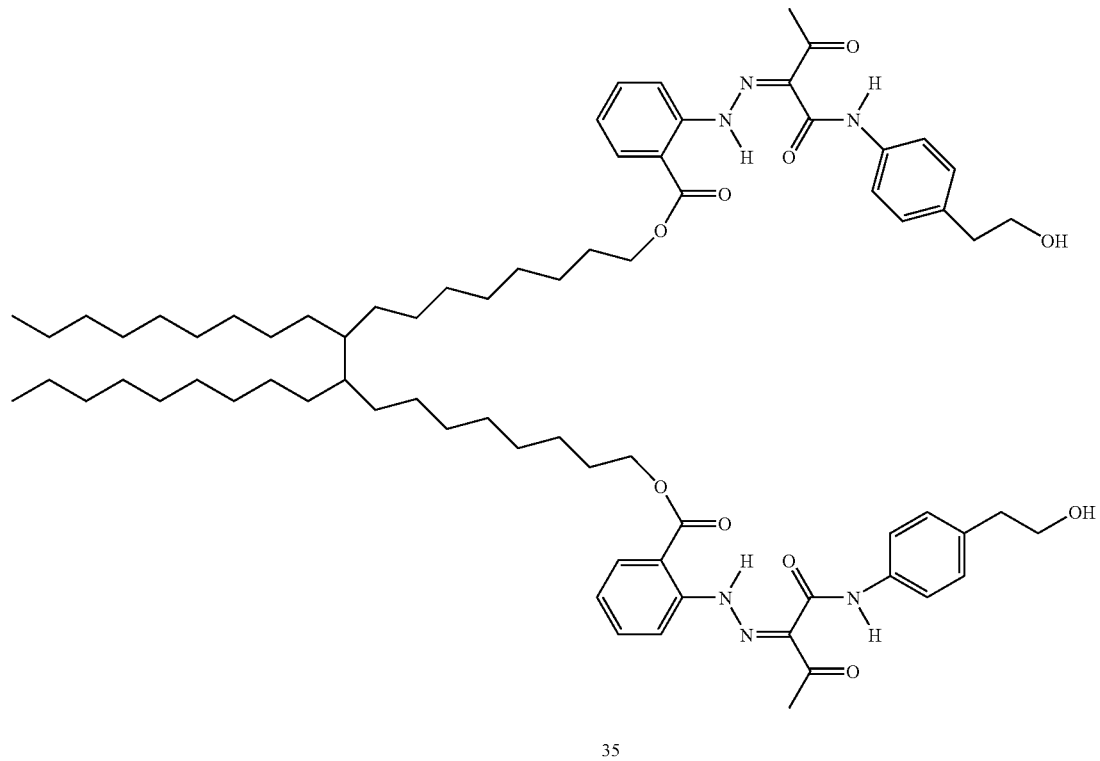

was prepared as follows.

Dissolving the p-hydroxyethylanilino-acetoacetamide. To a 4 liter beaker with magnetic stir bar was charged about 700 grams of deionized water, about 16.0 grams of acetic acid, and about 22.2 grams of sodium hydroxide. The contents were stirred until completely dissolved. About 700 milliliters of isopropyl alcohol and about 12.1 grams of p-hydroxyethylanilino-acetoacetamide from Example 4 above was then added and stirred until dissolved.

Adding the Dimer Dianthranilate Bis-Diazo to the Dissolved p-hydroxyethylanilino-acetoacetamide: The cooled contents from Example 5, Part A above were added to the beaker containing the p-hydroxyethylanilino-acetoacetamide solution. A yellow precipitate formed at the beginning of coupling, and then the solids turned into a very viscous liquid. After stirring for about one hour, the contents were allowed to settle over night. The top liquid was decanted. The bottom viscous liquid contained white salt and yellow product. About 700 milliliters of deionized water was added to the solids and stirred for about one hour. The aqueous layer was then discarded. The bottom yellow viscous liquid product was dissolved in about 300 milliliters of toluene and washed with water in a separatory funnel. The lower water layer was discarded and the top toluene layer was run through a silica plug. Then the toluene was evaporated yielding a viscous very dark yellow dye. The spectral strength of the yellow colorant was determined using a spectrophotometric procedure based on the measurement of the colorant in solution by dissolving the colorant in toluene and measuring the absorbance using a Perkin Elmer Lambda 2S UV/VIS spectrophotometer. The spectral strength of the colorant measured as about 32,363 ml* Absorbance Units per gram at absorption $\lambda_{max}$.

Example 9: Menthyl Anthranilate Diazotization

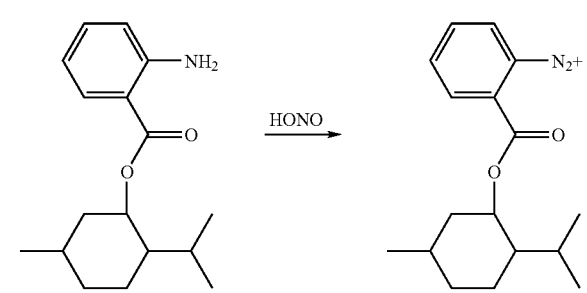

To a 150 milliliter 3-neck round bottom flask equipped with mechanical stirrer, salt/ice bath, and thermometer was charged about 11.9 grams of menthyl anthranilate (MW–275), about 29.7 grams of acetic acid, about 5.9 grams of water and about 1.5 grams of concentrated $H_2SO_4$. The contents were stirred until dissolved while keeping the temperature of the ice bath at about 0° C. About 16.5 grams of nitrosyl sulfuric acid (NSA MW=127, 40% by weight) was added slowly through an addition funnel maintaining the reaction temperature below about 3° C. The addition took about 32 minutes. The cooled reaction mixture was stirred an additional two hours and a PMA test was (to determine excess NO+) was run and the result was positive indicating the reaction was complete. About 1.8 grams of sulfamic acid was added (to react with excess NSA) and stirred for about 20 minutes. A PMA test confirmed that all excess NSA has been killed. At this point the reaction mixture is ready to couple.

Example 10: The Coupling of Menthyl Anthranilate Diazo to 2-ethylhexylacetoacetamide A compound of the formula

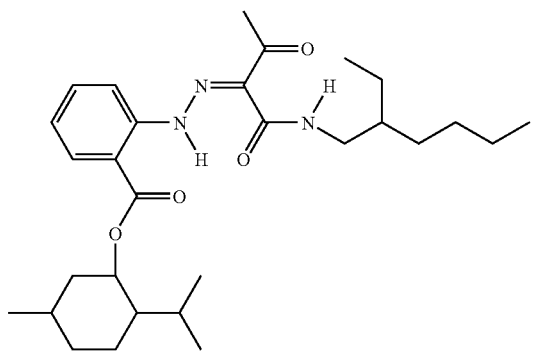

was prepared as follows.

Dissolving the 2-ethylhexylacetoacetamide. To a 1 liter beaker with magnetic stir bar was added about 100 grams of water, about 16 grams of acetic acid and about 22 grams of sodium hydroxide and stirred until everything was dissolved. About 700 milliliters of methanol was then added with stirring and the contents remained clear. About 9.3 grams of the acetoacetamide from Example 1 above was then added to the beaker. The solution remained clear. After stirring for several minutes the solution become cloudy. About 120 grams of additional water was added until the solution became clear again.

Adding the Menthyl Anthranilate Diazo to the Dissolved 2-Ethylhexylacetoacetamide. The cooled contents from Example 9 above were then slowly added to this solution allowing the azo coupling to take place. A yellow solids immediately began to precipitate out of solution. After stirring for about one hour the solids turned to oil with a lot of white salt. More water was added to the reaction contents until the salts dissolved. The contents were allowed to stir overnight. The aqueous layer was decanted and the remaining deep yellow oil was dissolved in toluene and washed with water in a separatory funnel. The bottom water layer was discarded while the top toluene layer was run through a silica gel plug. The solvent was evaporated. The spectral strength of the yellow colorant was determined using a spectrophotometric procedure based on the measurement of the colorant in solution by dissolving the colorant in toluene and measuring the absorbance using a Perkin Elmer Lambda 2S UV/VIS spectrophotometer. The spectral strength of the colorant measured as about 44,517 ml* Absorbance Units per gram at absorption $\lambda_{max}$.

Example 11: The coupling of Menthyl Anthranilate Diazo to dodecylacetoacetamide

A compound of the formula

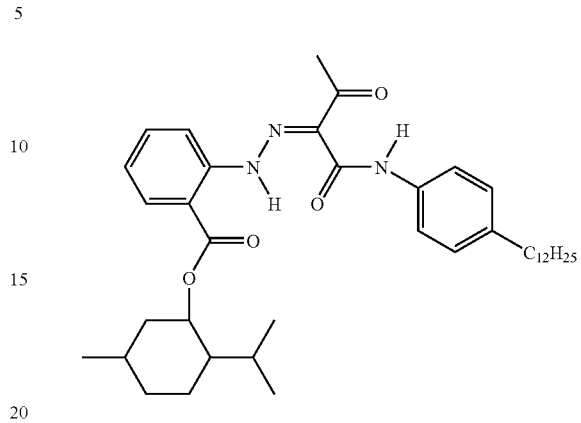

was prepared as follows.

Dissolving the dodecylanilineacetoacetamide: To a 1 liter beaker with magnetic stir bar was added about 100 grams of water, about 16 grams of acetic acid and about 22 grams of sodium hydroxide and stirred until everything was dissolved. About 700 milliliters of isopropyl alcohol was added and the solution became cloudy. An additional about 140 grams of water were added with stirring and the contents became clear. About 14.9 grams of the acetoacetamide from Example 2 above was then added to the beaker. The solution remained clear.

Adding the Menthyl Anthranilate Diazo to the Dissolved Dodecylanilino-acetoacetamide: The cooled contents from Example 9 above were then slowly added to this solution allowing the azo coupling to take place. An oily, gooey mass began to precipitate out of solution. The contents were allowed to stir overnight. The next day the water was decanted off and the gooey solid was dissolved in toluene was washed with water, separated, and the toluene layer run through a silica plug. The solvent was evaporated leaving a viscous oily yellow product. The spectral strength of the yellow colorant was determined using a spectrophotometric procedure based on the measurement of the colorant in solution by dissolving the colorant in toluene and measuring the absorbance using a Perkin Elmer Lambda 2S UV/VIS spectrophotometer. The spectral strength of the colorant measured as about 37,949 ml* Absorbance Units per gram at absorption $\lambda_{max}$.

Example 12

Preparation of an Ink Base

An ink base was prepared by melting, admixing, and filtering the following ingredients:

43.59 parts by weight polyethylene was (PE 655®obtained from Baker Petrolite) of the formula $CH_3(CH_2)_{50}CH_3$);

19.08 parts by weight stearyl stearamide was (KEMAMIDE® S-180, obtained from Crompton Corporation);

18.94 parts by weight tetra-amide resin obtained from the reaction of one equivalent of a C-36 dimer acid (obtained from Uniqema, New Castle, Del.) with two equivalents of etylene diamine and UNICID® 700 (obtained from Baker Petrolite), a long chain hydrocarbon having a terminal carboxylic acid group, prepared as described in Example 1 of U.S. Pat. No. 6,174,937, which is hereby incorporated by reference herein in its entirety.

11.71 parts by weight urethane resin obtained from the reaction of two equivalents of ABITOL® E hydroabietyl alcohol (obtained from Hercules Inc.) and one equivalent of isophorone diisocyanate, prepared as described in Example 1 of U.S. Pat. No. 5,782,966, which is hereby incorporated by reference herein;

6.48 parts by weight urethane resin that is the adduct of three equivalents of stearyl isocyanate and a glycerol-based alcohol, prepared as described in Example 4 of U.S. Pat. No. 6,309,453, which is hereby incorporated by reference herein in its entirety.

0.20 parts by weight NAUGUARD® 445 antioxidant (obtained from Uniroyal Chemical Co.).

Thereafter, 600 grams of the ink carrier components as listed above in the percentages as listed above were added to a 1 liter beaker and heated in an oven at 135° C. until molten. Subsequently, the beaker was inserted into a heating mantle set to 135° C. and the contents of the beaker were stirred for 45 minutes. The resulting ink was then filtered through a combination of Whatman #3 and 0.2 micron NAE filters and placed in a Mott filter assembly. Filtration was supported by the addition of 1 percent by weight FILTER-AID obtained from Fluka Chemika, and proceeded at a temperature of 135° C. until complete after 6 hours. The ink base was poured into molds containing about 31 grams of the colorless ink base and allowed to cool.

Example 13

Preparation of Ink Containing Colorant

About 29.9 grams of ink base from Example 12 was placed in a 100 milliliter beaker with a magnetic stir bar and subsequently placed in a 135° C. oil bath until molten. About 2.0 grams of the product of Example 6 above was then added and stirred for about 3 hours. The yellow colored ink was then poured into an aluminum mold.

Example 14

Printing of Ink Samples Containing Colorant

Printed samples of the ink prepared in Example 13 were generated on HAMMERMILL LASERPRINT® paper using a K Printing Proofer (manufactured by RK Print Coat Instrument Ltd., Litlington, Royston, Heris, SG8 0OZ, U.K.). In this method, the tested inks were melted onto a printing plate set at 150° C. temperature. A roller bar fitted with the paper was then rolled over the plate containing the melted ink on its surface. The ink on the paper was cooled, resulting in three separated image of rectangular blocks. The most intensely colored block contained the most ink deposited on the paper, and was therefore used to obtain the color value measurements. The printed samples were evaluated visually.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

The invention claimed is:

1. A compound of the formula

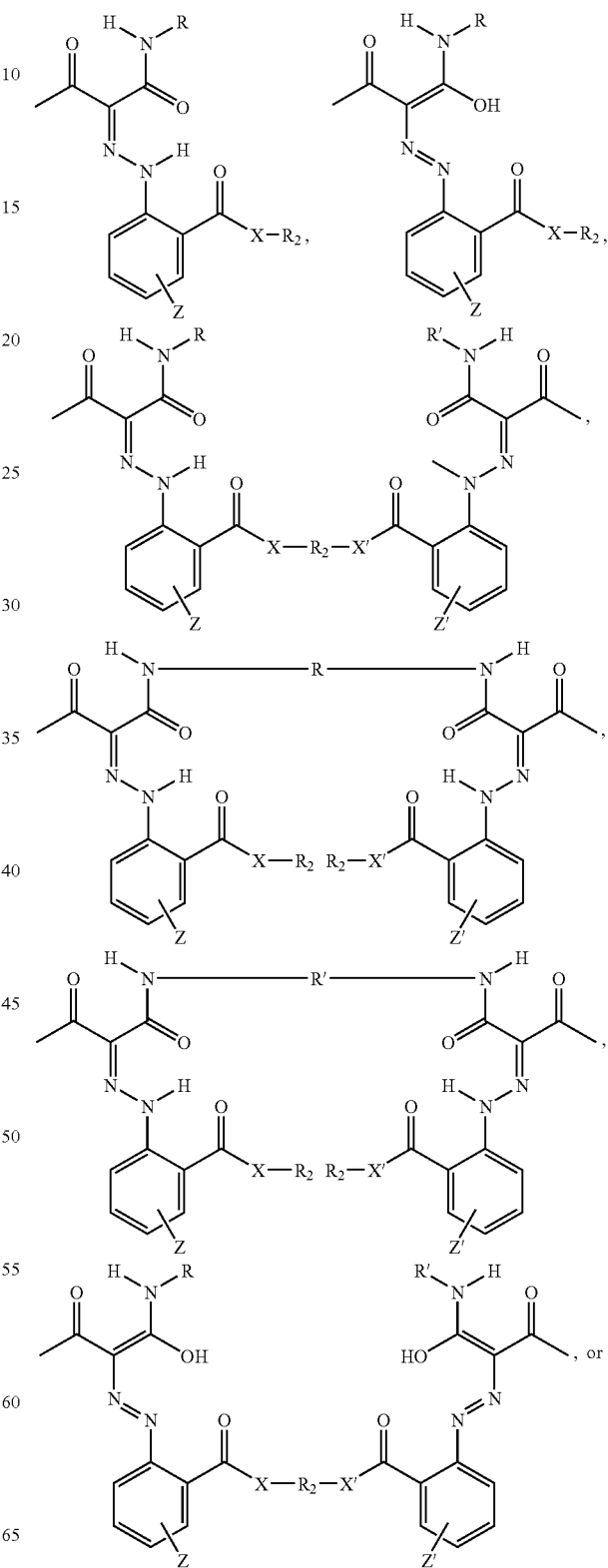

-continued

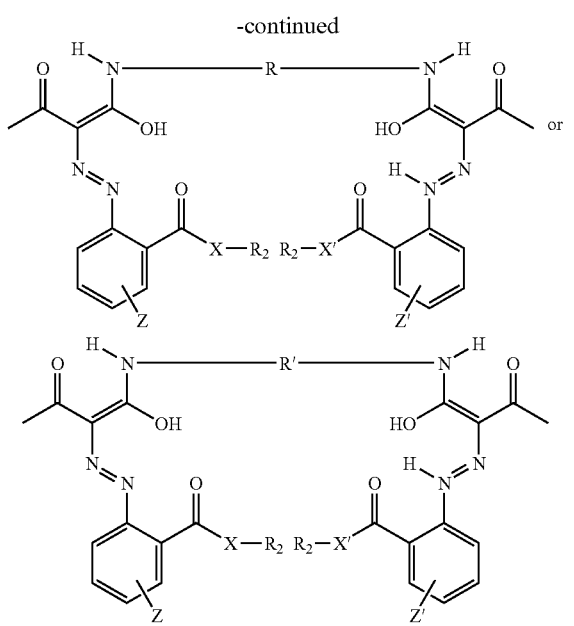

wherein substituent R, and R', if R' is present, on the acetoacetamido moiety is a 2-ethylhexyl, dodecylaniline, Guerbet, or p-hydroxyethylanilino moiety;

wherein $R_2$ is (i) an alkyl group, including substituted and unsubstituted alkyl groups, and wherein hetero atoms either may or may not be present in the alkyl group, (ii) an alkylene group, including substituted and unsubstituted alkylene groups, and wherein hetero atoms either may or may not be present in the alkylene group, (iii) an arylene group, including substituted and unsubstituted arylene groups, and wherein hetero atoms either may or may not be present in the arylene group (iv) an arylalkylene group, including substituted and unsubstituted arylalkylene groups, and wherein hetero atoms either may or may not be present in the arylalkylene group, (v) an alkylarylene group, including substituted and unsubstituted alkylarylene groups, and wherein hetero atoms either may or may not be present in the alkylarylene group, (vi) an alkyleneoxy group, including substituted and unsubstituted alkyleneoxy groups, and wherein hetero atoms either may or may not be present in the alkyleneoxy group, (vii) an aryleneoxy group, including substituted and unsubstituted aryleneoxy groups, and wherein hetero atoms either may or may not be present in the arylene oxy group, (viii) an arylalkyleneoxy group, including substituted and unsubstituted arylalkyleneoxy groups, and wherein hetero atoms either may or may not be present in the arylalkyleneoxy groups, (ix) an alkylaryleneoxy group, including substituted and unsubstituted alkylaryleneoxy groups, and wherein hetero atoms either may or may not be present in the alkylaryleneoxy group, (x) a polyalkyleneoxy group, (xi) a polyaryleneoxy group, (xii) a polyarylalkyleneoxy group, (xiii) a polyalkylaryleneoxy group, (xiv) a heterocyclic group, (xv) a silylene group, (xvi) a siloxane group, (xvii) a polysilylene group, or (xviii) a polysiloxane group;

wherein X and X', if X' is present, is a (i) direct bond, (ii) an oxygen atom, (iii) a nitrogen atom, (iv) a sulfur atom, (v) a group of the formula $-NR_{40}-$ wherein $R_{40}$ is a hydrogen atom, an alkyl group, including substituted and unsubstituted alkyl groups, and wherein hetero atoms either may or may not be present in the alkyl group, an aryl group, including substituted and unsubstituted aryl groups, and wherein hetero atoms either may or may not be present in the aryl group, an arylalkyl group, including substituted and unsubstituted arylalkyl groups, and wherein hetero atoms either may or may not be present in the arylalkyl group, or an alkylaryl group, including substituted and unsubstituted alkylaryl groups, and wherein hetero atoms either may or may not be present in the alkylaryl group, (vi) or a group of the formula $-CR_{50}R_{60}-$; wherein $R_{50}$ and $R_{60}$ each, independently of the other, is a hydrogen atom, an alkyl group, including substituted and unsubstituted alkyl groups, and wherein hetero atoms either may or may not be present in the alkyl group, an aryl group, including substituted and unsubstituted aryl groups, and wherein hetero atoms either may or may not be present in the aryl group, an arylalkyl group, including substituted and unsubstituted arylalkyl groups, and wherein hetero atoms either may or may not be present in the arylalkyl group, or an alkylaryl group, including substituted and unsubstituted alkylaryl groups, and wherein hetero atoms either may or may not be present in the alkylaryl group, wherein two or more substituents can be joined together to form a ring, and wherein X and X' can be the same as each other or different from each other;

wherein Z and Z' are each optionally present and if present are each independently selected from a (i) hydrogen atom, (ii) a halogen atom, (iii) a nitro group, (iv) an alkyl group, including substituted and unsubstituted alkyl groups, and wherein hetero atoms either may or may not be present in the alkyl group, (v) an aryl group, including substituted and unsubstituted aryl groups, and wherein hetero atoms either may or may not be present in the aryl group, (vi) an arylalkyl group, including substituted and unsubstituted arylalkyl groups, and wherein hetero atoms either may or may not be present in the arylalkyl group, (vii) an alkylaryl group, including substituted and unsubstituted alkylaryl groups, and wherein hetero atoms either may or may not be present in the alkylaryl group, (viii) a group of the formula

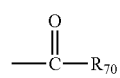

wherein $R_{70}$ is an alkyl group, including substituted and unsubstituted alkyl groups, and wherein hetero atoms either may or may not be present in the alkyl group, an aryl group, including substituted and unsubstituted aryl groups, and wherein hetero atoms either may or may not be present in the aryl groups, an arylalkyl group, including substituted and unsubstituted arylalkyl groups, and wherein hetero atoms either may or may not be present in the arylalkyl group, an alkylaryl group, including substituted and unsubstituted alkylaryl groups, and wherein hetero atoms either may or may not be present in the alkylaryl group, an alkoxy group, including substituted and unsubstituted alkoxy groups, and wherein hetero atoms either may or may not be present in the alkoxy group, an aryloxy group, including substituted and unsubstituted aryloxy groups, and wherein hetero atoms either may or may not be present in the aryloxy group, an arylalkyloxy group, including substituted and unsubstituted alkylaryloxy groups, and wherein hetero atoms either may or may not be present in the alkylaryloxy group, an alkylaryloxy group, including substituted and unsubstituted alkylaryloxy groups, and wherein hetero atoms either may or may not be present in the alkylaryloxy group, a polyalkyleneoxy group, a polyaryleneoxy group, a heterocyclic group, a silyl group, a siloxane group, a polysilylene group, or a polysiloxane group, (ix) a sulfonyl group of the formula —SO$_2$R$_{80}$ wherein R$_{80}$ is a hydrogen atom, an alkyl group, including substituted and unsubstituted alkyl groups, and wherein hetero atoms either may or may not be present in the alkyl group, an aryl group, including substituted and unsubstituted aryl groups, and wherein hetero atoms either may or may not be present in the aryl group, an arylalkyl group, including substituted and unsubstituted arylalkyl groups, and wherein hetero atoms either may or may not be present in the arylalkyl group, an alkylaryl group, including substituted and unsubstituted alkylaryl groups, and wherein hetero atoms either may or may not be present in the alkylaryl group, an alkoxy group, including substituted and unsubstituted alkoxy groups, and wherein hetero atoms either may or may not be present in the alkoxy group, an aryloxy group, including substituted and unsubstituted aryloxy groups, and wherein hetero atoms either may or may not be present in the aryloxy group, an arylalkyloxy group, including substituted and unsubstituted arylalkyloxy groups, and wherein hetero atoms either may or may not be present in the arylalkyloxy group, an alkylaryloxy group, including substituted and unsubstituted alkylaryloxy groups, and wherein hetero atoms either may or may not be present in the alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, or (x) a phosphoryl group of the formula —PO$_3$R$_{90}$ wherein R$_{90}$ is a hydrogen atom, an alkyl group, including substituted and unsubstituted alkyl groups, and wherein hetero atoms either may or may not be present in the alkyl group, an aryl group, including substituted and unsubstituted aryl groups, and wherein hetero atoms either may or may not be present in the aryl group, an arylalkyl group, including substituted and unsubstituted arylalkyl groups, and wherein hetero atoms either may or may not be present in the arylalkyl group, an alkylaryl group, including substituted and unsubstituted alkylaryl groups, and wherein hetero atoms either may or may not be present in the alkylaryl group, an alkoxy group, including substituted and unsubstituted alkoxy groups, and wherein hetero atoms either may or may not be present in the alkoxy group, an aryloxy group, including substituted and unsubstituted aryloxy groups, and wherein hetero atoms either may or may not be present in the aryloxy group, an arylalkyloxy group, including substituted and unsubstituted arylalkyloxy groups, and wherein hetero atoms either may or may not be present in the arylalkyloxy group, an alkylaryloxy group, including substituted and unsubstituted alkylaryloxy groups, and wherein hetero atoms either may or may not be present in the alkylaryloxy group, a polyalkyleneoxy group, a polyaryleneoxy group, a polyarylalkyleneoxy group, a polyalkylaryleneoxy group, a heterocyclic group, a silyl group, a siloxane group, a polysilylene group, or a polysiloxane group, wherein two or more substituents can be joined together to form a ring, and wherein Z and Z' can be the same as each other or different from each other; and wherein Z and X can be joined together to form a ring and wherein Z' and X' can be joined together to form a ring.

2. A compound according to claim 1, wherein R$_2$ is a linear alkylene group.

3. A compound according to claim 1, wherein R$_2$ is a branched alkylene group.

4. A compound according to claim 1, wherein R$_2$ is a saturated alkylene group.

5. A compound according to claim 1, wherein R$_2$ is an unsaturated alkylene group.

6. A compound according to claim 1, wherein R$_2$ is an unsubstituted alkylene group.

7. A compound according to claim 1, wherein R$_2$ is a substituted alkylene group.

8. A compound according to claim 1, wherein R$_2$ is an alkylene group with at least about 10 carbon atoms.

9. A compound according to claim 1, wherein R$_2$ is an alkylene group with about 36 carbon atoms.

10. A compound according to claim 1, wherein R$_2$ is

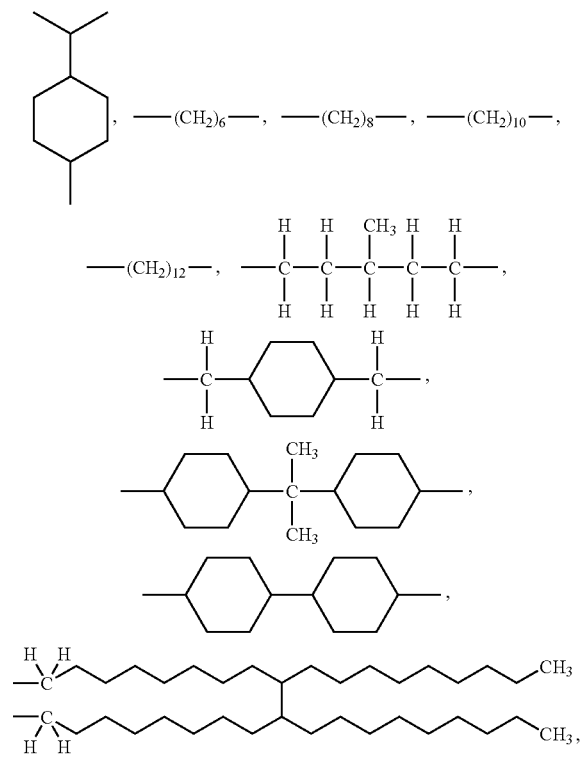

-continued
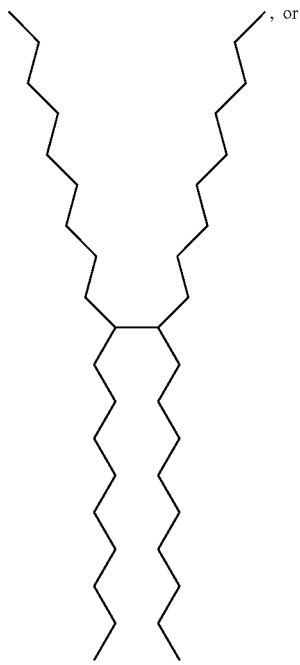, or
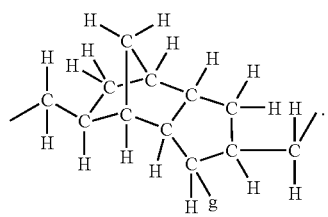
11. A compound according to claim 1, wherein $R_2$ is a branched alkylene group having 36 carbon atoms which may include unsaturations and cyclic groups.
12. A compound according to claim 1, of the formula
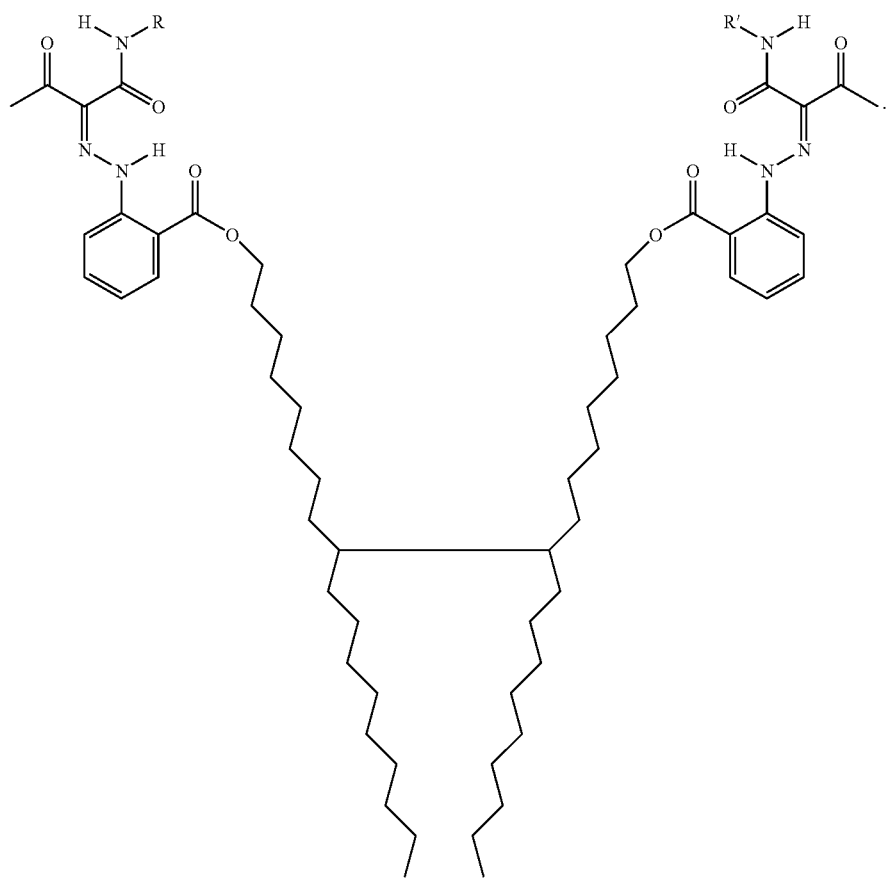

13. A compound according to claim 1, of the formula
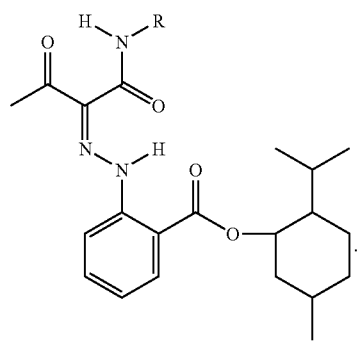
14. A compound according to claim 1, of the formula
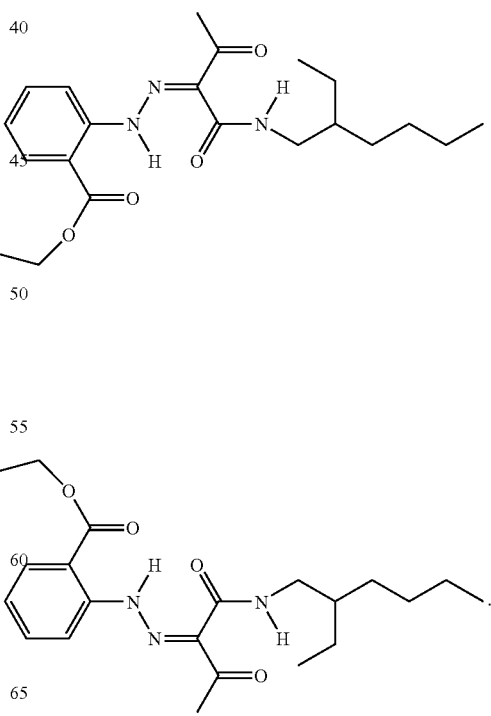

15. A compound according to claim 1, of the formula
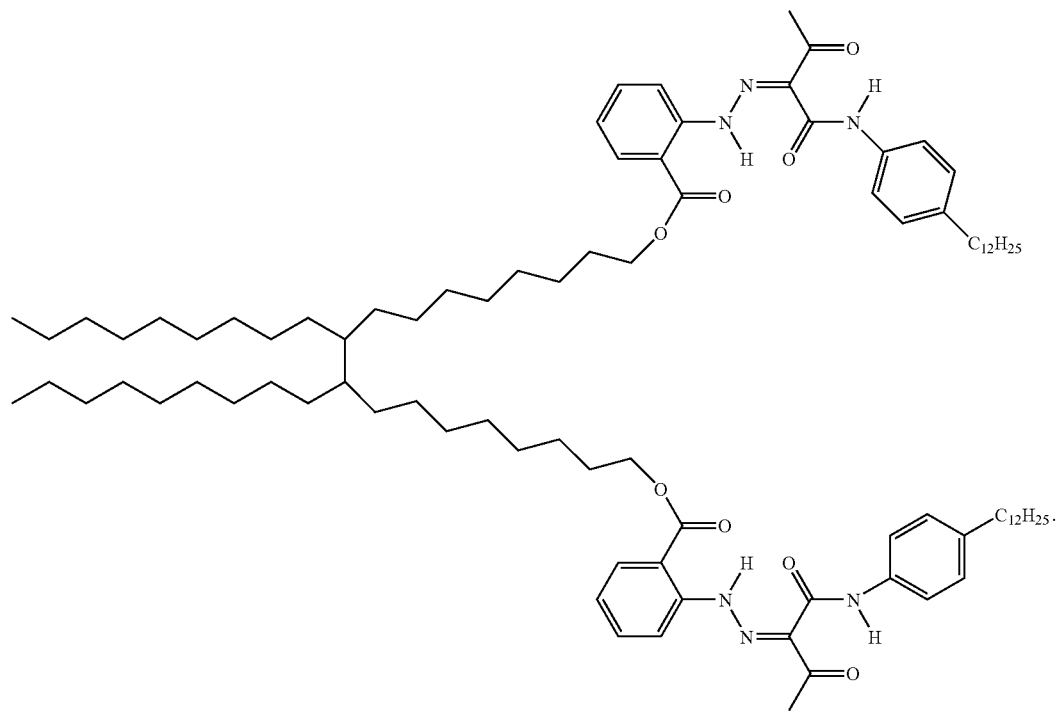
16. A compound according to claim 1, of the formula
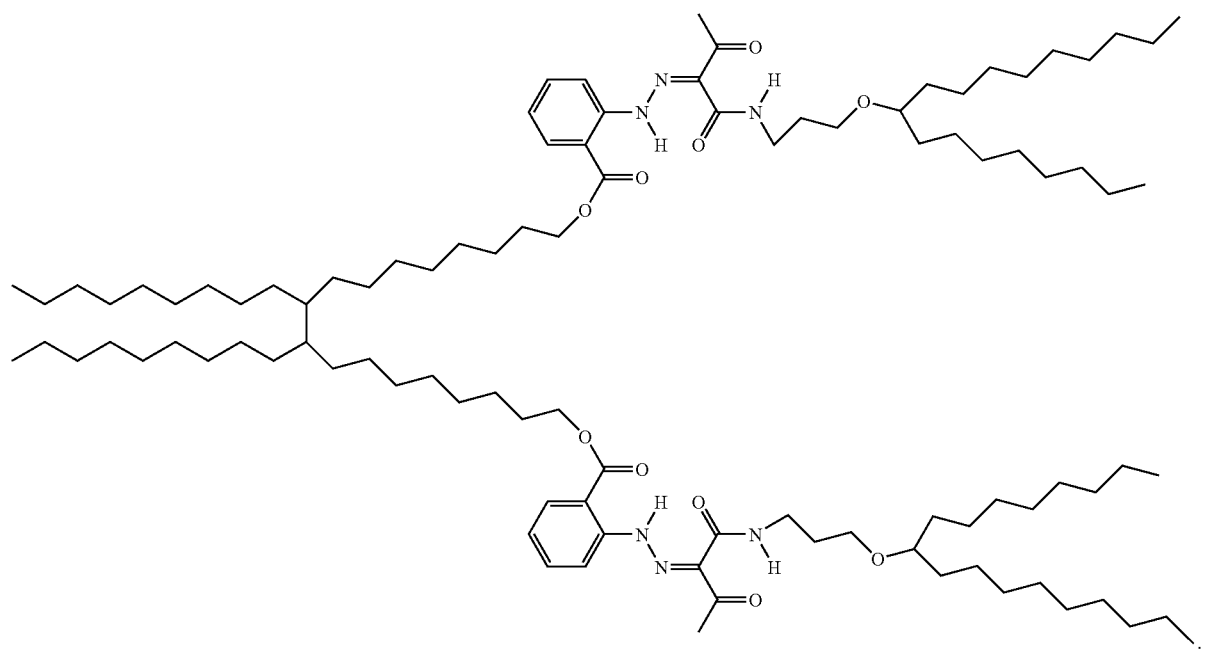

17. A compound according to claim 1, of the formula
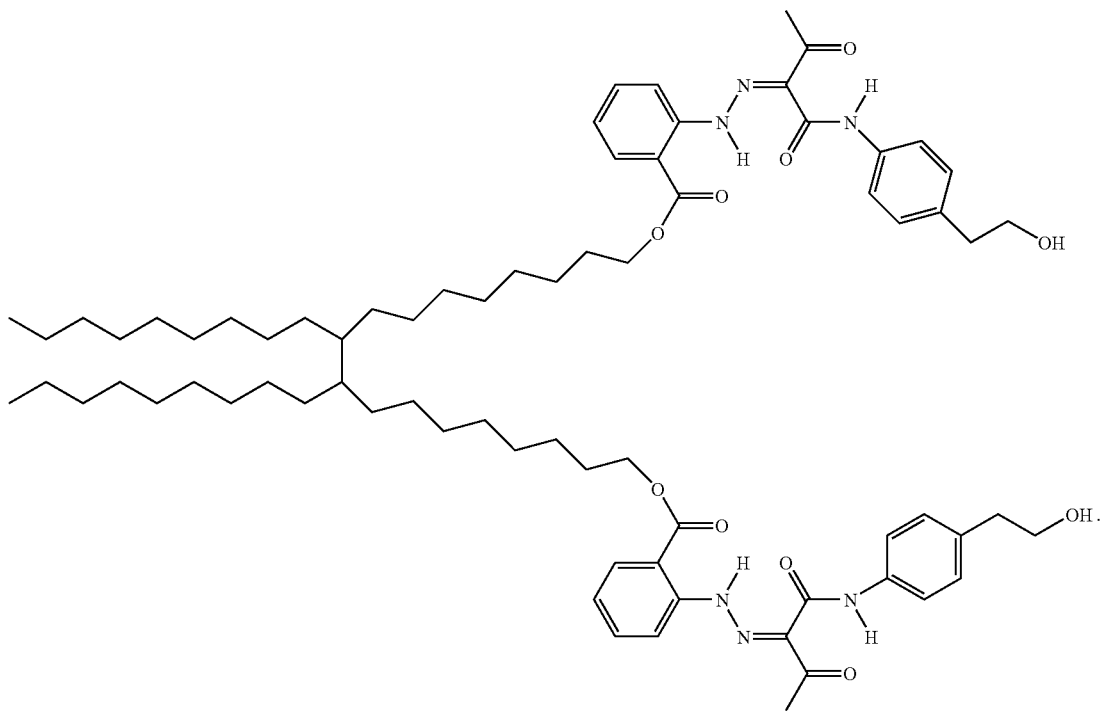
18. A compound according to claim 1, of the formula
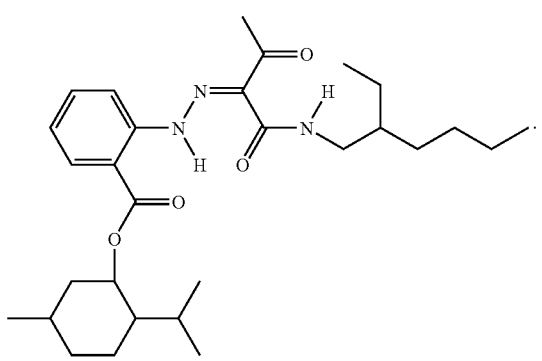
19. A compound according to claim 1, of the formula
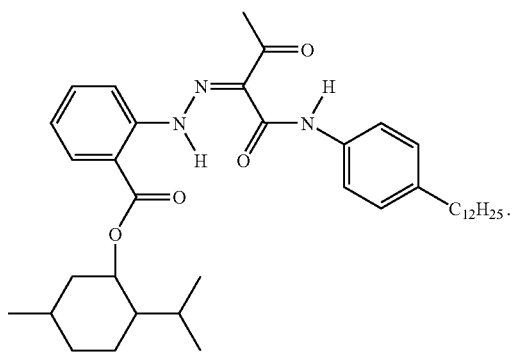
* * * * *